United States Patent [19]

Tsushima et al.

[11] Patent Number: 5,464,829
[45] Date of Patent: Nov. 7, 1995

[54] CEPHALOSPORIN DERIVATIVES

[75] Inventors: Masaki Tsushima; Yuko Kano; Katsuyoshi Iwamatsu; Atsushi Tamura; Seiji Shibahara, all of Kanagawa, Japan

[73] Assignee: Meiji Seika Kaisha Ltd., Tokyo, Japan

[21] Appl. No.: 167,204

[22] Filed: Dec. 16, 1993

[30] Foreign Application Priority Data

Dec. 18, 1992 [JP] Japan .................................. 4-339267
Aug. 3, 1993 [JP] Japan .................................. 5-192403

[51] Int. Cl.$^6$ ..................... C07D 501/36; A61K 31/545
[52] U.S. Cl. ..................... 514/206; 540/227; 540/225
[58] Field of Search ................. 540/226, 227; 514/206, 202, 203

[56] References Cited

U.S. PATENT DOCUMENTS

| | | | |
|---|---|---|---|
| 4,388,314 | 6/1983 | Nannini et al. | 540/226 |
| 4,988,687 | 1/1991 | Nakagawa et al. | 540/227 |
| 5,247,073 | 9/1993 | Ternansky | 540/227 |

OTHER PUBLICATIONS

Chemical Abstracts vol. 122:31198 (1995).
Chemical Abstracts vol. 108:221493 (1988).

*Primary Examiner*—Nicholas Rizzo
*Attorney, Agent, or Firm*—Sughrue, Mion, Zinn, Macpeak & Seas

[57] ABSTRACT

A cephalosporin derivative having a quaternary salt type substituent group at the 3-position, represented by formula (I):

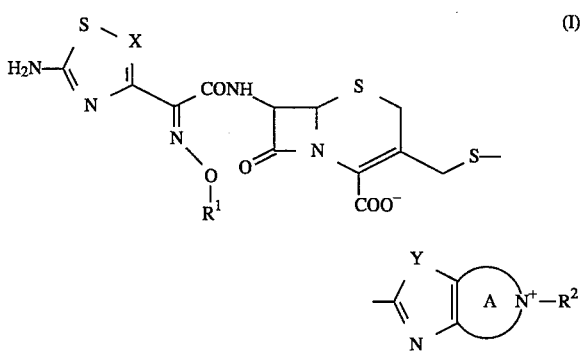

wherein X is a carbon atom or a nitrogen atom; Y is a sulfur atom, an oxygen atom or a nitrogen atom substituted with a substituted or unsubstituted lower alkyl group; $R^1$ is a hydrogen atom, a lower alkyl group or a substituted lower alkyl group; $R^2$ is a lower alkyl group, a substituted lower alkyl group, a lower alkylene group or a substituted lower alkylene group; and A is an unsaturated six-membered heterocyclic ring containing at least one nitrogen atom, or a pharmaceutically acceptable salt thereof is disclosed. The derivatives have excellent antibacterial activities and can be used as a drug for the treatment of various bacterial infections.

4 Claims, No Drawings

CEPHALOSPORIN DERIVATIVES

FIELD OF THE INVENTION

This invention relates to novel cephalosporin derivatives which have a quaternary salt type substituent group at the 3-position. More particularly, it relates to cephalosporin derivatives which have a strong antibacterial activity and a broad antibacterial spectrum.

BACKGROUND OF THE INVENTION

Cephalosporin antibiotics are markedly effective drugs for the treatment of infectious diseases in mammals in view of their excellent antibacterial activities and low toxicity against mammals. In recent years, a number of cephalosporin derivatives having an aminothiazolylacetyl group at the 7-position of the cephem ring have been studied and developed since they show strong antibacterial activities and high stability against β-lactamase.

In various countries, many studies have addressed so-called "onium salt type cephalosporin antibiotics" such as ceftazidime and cefpirome which have an aminothiazolylacetyl group and a quaternary salt type substituent group at the 7-position and the 3-position, respectively and exert strong antibacterial activities and broad antibacterial spectrum ranging from gram-positive bacteria to *Pseudomonas aeruginosa*. However, these onium salt type cephalosporin antibiotics including ceftazidime and cefpirome are still unsatisfactory in terms of their antibacterial activities upon *Pseudomonas aeruginosa* and gram-positive bacteria including *Staphylococcus aureus* which have recently been given attention in a clinical viewpoint. Thus, great concern has been directed toward the development of novel cephalosporin antibiotics having improved antibacterial activities upon these bacteria.

SUMMARY OF THE INVENTION

An object of the present invention is to provide novel cephalosporin derivatives having strong antibacterial activities on various pathogenic bacteria.

The present inventors have conducted intensive studies in order to develop novel cephalosporin derivatives which have strong antibacterial activities and broad antibacterial spectrum. As a result, the inventors have succeeded in synthesizing novel cephalosporin derivatives represented by the following formula (I) which exhibit excellent antibacterial activities and broad antibacterial spectrum.

Thus, the present invention provides a cephalosporin derivative represented by formula (I):

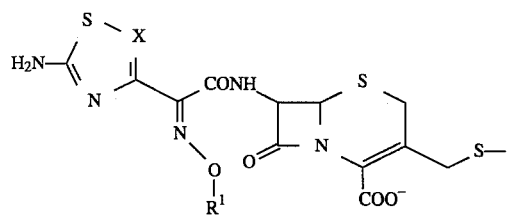

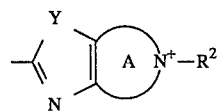

wherein X is a carbon atom or a nitrogen atom; Y is a sulfur atom, an oxygen atom or a nitrogen atom substituted with a substituted or unsubstituted lower alkyl group; $R^1$ is a hydrogen atom, a lower alkyl group or a substituted lower alkyl group; $R^2$ is a lower alkyl group, a substituted lower alkyl group, a lower alkylene group or a substituted lower alkylene group; and A is an unsaturated six-membered heterocyclic ring which contains at least one nitrogen atom, or a salt thereof.

The present invention further provides an antibacterial composition comprising the cephalosporin derivative or a pharmaceutically acceptable salt thereof as an active ingredient and a pharmaceutically acceptable carrier.

DETAILED DESCRIPTION OF THE INVENTION

In the definition of formula (I), the term "lower alkyl group" or "lower alkylene group" means a straight or branched alkyl or alkylene group having 1 to 4 carbon atoms. Specific examples of substituent groups in the substituted lower alkyl and lower alkylene groups in formula (I) include a halogen atom (fluorine, chlorine, bromine or iodine), a hydroxyl group, a carboxyl group, a carbamoyl group, an amino group, a lower alkylamino group having 1 to 4 carbon atoms and these groups substituted with a lower alkyl group having 1 to 4 carbon atoms, a lower alkylene group having 1 to 4 carbon atoms, an aralkyl group having 7 to 10 carbon atoms and the like.

The A ring may contain other hetero atoms as long as it is an unsaturated six-membered heterocyclic ring which contains at least one nitrogen atom. Specific examples thereof include unsaturated heterocyclic rings having only nitrogen atom(s) as a hetero atom, such as pyridine ring, pyrimidine ring, pyrazine ring, pyridazine ring and their dihydro or tetrahydro derivatives, and other nitrogen atom-containing unsaturated heterocyclic rings further having sulfur, oxygen or the like hetero atom, such as thiazine ring, thiadiazine ring, oxazine ring, oxadiazine ring and the like.

Examples of the cephalosporin derivatives of the present invention represented by formula (I) are given below by way of illustration and not by way of limitation.

1. 7-{(Z)-2-(2-aminothiazol-4-yl)-2-methoxyiminoacetamido}-3-(5-methylthiazolo[4,5-c]pyridinium-2-yl)thiomethyl-3-cephem-4-carboxylate
2. 7-{(Z)-2-(2-aminothiazol-4-yl)-2-methoxyiminoacetamido}-3-(4-methylthiazolo[4,5-b]pyridinium-2-yl)thiomethyl-3-cephem-4-carboxylate
3. 7-{(Z)-2-(2-aminothiazol-4-yl)-2-carboxymethoxyiminoacetamido}-3-(5-methylthiazolo[4,5-c]pyridinium-2-yl)thiomethyl-3-cephem-4-carboxylate
4. 7-{(Z)-2-(2-aminothiazol-4-yl)-2-(1-carboxy-1-methylethoxyimino)acetamido}-3-(5-methylthiazolo[4,5-c]pyridinium-2-yl)thiomethyl-3-cephem-4-carboxylate
5. 7-[(Z)-2-(2-aminothiazol-4-yl)-2-{(S)-1-carboxyethoxyimino}acetamido]-3-(5-methylthiazolo[4,5-c]pyridinium-2-yl)thiomethyl-3-cephem-4-carboxylate
6. 7-{(Z)-2-(5-aminothiadiazol-3-yl)-2-methoxyiminoacetamido}-3-(5-methylthiazolo[4,5-c]pyridinium-2-yl)thiomethyl-3-cephem-4-carboxylate 7. 7-{(Z)-2-(5-aminothiazol-3-yl)-2-(1-carboxy-1-methylethoxyimino)acetamido}-3-(5-methylthiazolo[4,5-c]Pyridinium-2-yl)thiomethyl-3-cephem-4-carboxylate
8. 7-{(Z)-2-(2-aminothiazol-4-yl)-2-carboxymethoxyiminoacetamido}-3-(4-methylthiazolo[4,5-b]pyridinium-2-yl)thiomethyl-3-cephem-4-carboxylate
9. 7-{(Z)-2-(2-aminothiazol-4-yl)-2-(1-carboxy-1-methylethoxyimino)acetamido}-3-(4-methylthiazolo[4,5-b]Pyridinium-2-yl)thiomethyl-3-cephem-4-carboxylate
10. 7-[(Z)-2-(2-aminothiazol-4-yl)-2-{(S)-1-carboxyethoxyimino}acetamido]-3-(4-methylthiazolo[4,5-b]Pyridinium-2-yl)thiomethyl-3-cephem-4-carboxylate
11. 7-{(Z)-2-(2-aminothiazol-4-yl)-2-methoxyiminoacetamido}-3-(5-methylthiazolo[5,4-c]pyridinium-2-yl)thiomethyl-3-cephem-4-carboxylate
12. 7-{(Z)-2-(2-aminothiazol-4-yl)-2-carboxymethoxyiminoacetamido}-3-(5-methylthiazolo[5,4-c]pyridinium-2-yl)thiomethyl-3-cephem-4-carboxylate
13. 7-{(Z)-2-(2-aminothiazol-4-yl)-2-(1-carboxy-1methylethoxyimino)acetamido}-3-(5-methylthiazolo[5,4-c]pyridinium-2-yl)thiomethyl-3-cephem-4-carboxylate
14. 7-[(Z)-2-(2-aminothiazol-4-yl)-2-{(S)-1-carboxyethoxyimino}acetamido]-3-(5-methylthiazolo[5,4-c]pyridinium-2-yl)thiomethyl-3-cephem-4-carboxylate
15. 7-{(Z)-2-(2-aminothiazol-4-yl)-2-methoxyiminoacetamido}-3-(4-methylthiazolo[5,4-b]pyridinium-2-yl)thiomethyl-3-cephem-4-carboxylate
16. 7-{(Z)-2-(2-aminothiazol-4-yl)-2-carboxymethoxyiminoacetamido}-3-(4-methylthiazolo[5,4-b]pyridinium-2-yl)thiomethyl-3-cephem-4-carboxylate
17. 7-{(Z)-2-(2-aminothiazol-4-yl)-2-(1-carboxy-1-methylethoxyimino)acetamido}-3-(4-methylthiazolo[5,4-b]pyridinium-2-yl)thiomethyl-3-cephem-4-carboxylate
18. 7-[(Z)-2-(2-aminothiazol-4-yl)-2-{(S)-1-carboxyethoxyimino}acetamido]-3-(4-methylthiazolo[5,4-b]pyridinium-2-yl)thiomethyl-3-cephem-4-carboxylate
19. 7-{(Z)-2-(2-aminothiazol-4-yl)-2-methoxyiminoacetamido}-3-(5-carboxymethylthiazolo[4,5-c]pyridinium-2-yl)thiomethyl-3-cephem-4-carboxylate
20. 7-[(Z)-2-(2-aminothiazol-4-yl)-2-{(S)-1-carboxyethoxyimino}acetamido]-3-(5-ethylthiazolo[4,5-c]pyridinium-2-yl)thiomethyl-3-cephem-4-carboxylate
21. 7-{(Z)-2-(2-aminothiazol-4-yl)-2-(1-carboxy-1-methylethoxyimino)acetamido}-3-(5-ethylthiazolo[4,5-c]pyridinium-2-yl)thiomethyl-3-cephem-4-carboxylate
22. 7-[(Z)-2-(2-aminothiazol-4-yl)-2-{(S)-1-carboxyethoxyimino}acetamido]-3-{5-(2-fluoroethyl)thiazolo[4,5-c]pyridinium-2-yl)thiomethyl-3-cephem-4-carboxylate
23. 7-{(Z)-2-(2-aminothiazol-4-yl)-2-(1-carboxy-1-methylethoxyimino)acetamido}-3-{5-(2-fluoroethyl)thiazolo[4,5-c]pyridinium-2-yl)thiomethyl-3-cephem-4-carboxylate
24. 7-[(Z)-2-(2-aminothiazol-4-yl)-2-{(S)-1-carboxyethoxyimino}acetamido]-3-{5-(2-hydroxyethyl)thiazolo[4,5-c]pyridinium-2-yl)thiomethyl-3-cephem-4-carboxylate
25. 7-{(Z)-2-(2-aminothiazol-4-yl)-2-(1-carboxy-1-methylethoxyimino)acetamido}-3-{5-(2-hydroxyethyl)thiazolo[4,5-c]pyridinium-2-yl)thiomethyl-3-cephem-4-carboxylate
26. 7-[(Z)-2-(2-aminothiazol-4-yl)-2-{(S)-1-carboxyethoxyimino}acetamido]-3-(5-carbamoylmethylthiazolo[4,5-c]pyridinium-2-yl)thiomethyl-3-cephem-4-carboxylate
27. 7-{(Z)-2-(2-aminothiazol-4-yl)-2-(1-carboxy-1-methylethoxyimino)acetamido}-3-(5-carbamoylmethylthiazolo[4,5-c]pyridinium-2-yl)thiomethyl-3-cephem-4-carboxylate
28. 7-{(Z)-2-(2-aminothiazol-4-yl)-2-methoxyiminoacetamido}-3-(5-methyloxazolo[4,5-c]pyridinium-2-yl)thiomethyl-3-cephem-4-carboxylate
29. 7-{(Z)-2-(2-aminothiazol-4-yl)-2-carboxymethoxyiminoacetamido}-3-(5-methyloxazolo[4,5-c]pyridinium-2-yl)thiomethyl-3-cephem-4-carboxylate
30. 7-[(Z)-2-(2-aminothiazol-4-yl)-2-{(S)-1-carboxyethoxyimino}acetamido]-3-(5-methyloxazolo[4,5-c]pyridinium-2-yl)thiomethyl- 3-cephem-4-carboxylate
31. 7-{(Z)-2-(5-aminothiazol-3-yl)-2-methoxyiminoacetamido}-3-(5-(2-methyloxazolo[4,5-c]pyridinium-2-yl)thiomethyl-3-cephem-4-carboxylate
32. 7-[(Z)-2-(2-aminothiazol-4-yl)-2-{(S)-1-carboxyethoxyimino}acetamido]-3-(5-methylthiazolo[4,5-d]pyridazinium-2-yl)thiomethyl-3-cephem-4-carboxylate
33. 7-[(Z)-2-(2-aminothiazol-4-yl)-2-{(S)-1-carboxyethoxyimino}acetamido]-3-(5,5-dimethyl-4H,6H,7H-thiazolo[5,4-c]pyridinium-2-yl)thiomethyl-3-cephem-4-carboxylate
34. 7-[(Z)-2-(2-aminothiazol-4-yl)-2-{(S)-1-carboxyethoxyimino}acetamido]-3-(1,5-dimethylimidazolo[4,5-c]pyridinium-2-yl)thiomethyl- 3-cephem-4-carboxylate The compound of formula (I) of the present invention may be in the form of a pharmaceutically acceptable salt such as sodium, hydrochloride, sulfate or the like.

Though the compound of formula (I) of the present invention can be produced by various means, it is convenient to produce it in accordance with process (A) which comprises steps 1 to 3, process (B) which comprises steps (a) to (d) or process (C) which comprises steps i to ii, as diagrammatically shown below with respective reaction schemes.

Production process (A)

Step 1

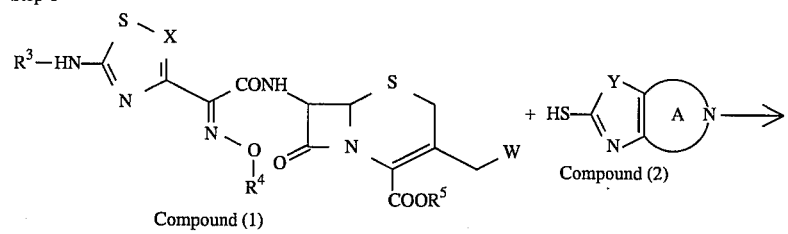

Compound (1)     Compound (2)

-continued

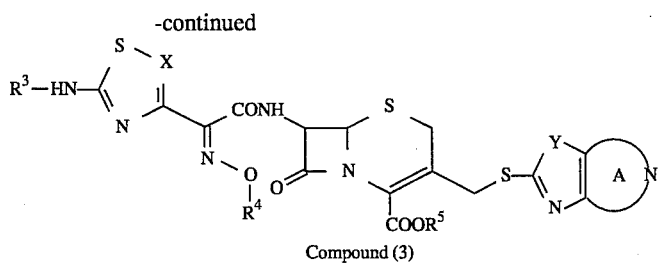
Compound (3)

Step 2

Compound (3) + R²—W ⟶
Compound (4)

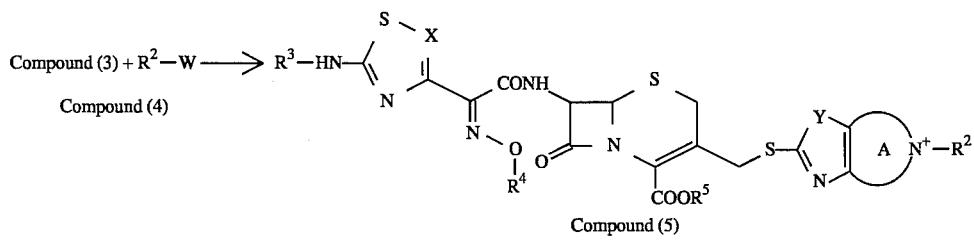
Compound (5)

Step 3

Compound (5) ⟶
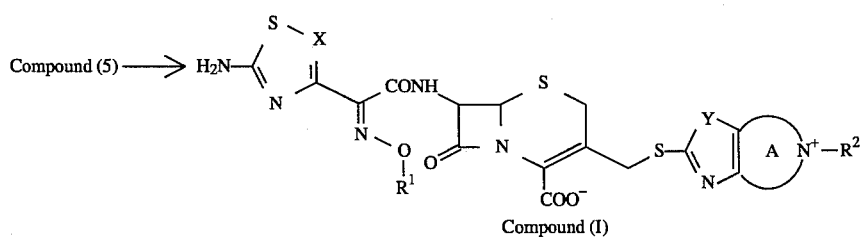
Compound (I)

In the compounds (1) to (5) and (I) shown in the above respective schemes, each of $R^1$, $R^2$, X and Y has the same meaning as described in formula (I) of the present invention.

The starting compound (1) can be synthesized in accordance with the method well known in the art as described in J. Antibiot., 44, 1371 (1991), ibid., 38, 1738 (1985), J. Med. Chem., 33, 77 (1990), JP-A-60-78987 and JP-A-58-222092 (the term "JP-A" used herein means an unexamined published Japanese patent application).

In the starting compound (1) to be used in the step 1 of the above production process (A), $R^3$ is an amino protective group such as a trityl group, a chloroacetyl group, a formyl group or the like, $R^4$ is the same group of $R^1$ or an oxime protective group such as a trityl group and $R^5$ is a carboxyl protective ester-forming group such as a diphenylmethyl group, a benzyl group, a p-methoxybenzyl group, a p-nitrobenzyl group, a tert-butyl group, an allyl group, a 2,2,2-trichloroethyl group or, the like. W in the starting compound (1) is a leaving group such as a halogen atom (chlorine, bromine or iodine), a diphenylphosphoryloxy group, a methanesulfonyloxy group, a p-toluenesulfonyloxy group, a trifluoromethanesulfonyloxy group or the like. The deprotection of the compound of formula (I) in which $R^4$ is an oxime protective group gives the compound of formula (I) in which $R^1$ is hydrogen.

The steps 1 to 3 of the production process (A) shown above can be carried out as follows.

In the step 1, a starting compound (1) is allowed to undergo a substitution reaction in an anhydrous organic solvent with a compound (2) or its sodium salt to obtain a compound (3). The molar ratio of the compound (2) to the compound (1) ranges from 1.1 to 2.0, preferably 1.2 to 1.5. Preferred examples of the reaction solvent include chloroform, dichloromethane, tetrahydrofuran, N,N-dimethylformamide, acetonitrile, hexamethylphosphate triamide and the like. The reaction may be effected at a temperature of preferably from −20° to 50° C. for 1 to 4 hours. After completion of the reaction, the reaction mixture is subjected to usual after-treatments comprising, for example, putting the reaction mixture into water, effecting extraction with a solvent into which the compound (3) can be dissolved, such as chloroform, dichloromethane or ethyl acetate, washing the organic layer with water, drying the organic layer with a drying agent and removing the solvent under reduced pressure. If necessary, the thus obtained compound (3) is purified by means of silica gel column chromatography, crystallization and the like.

In the step 2, the compound (3) is allowed to react with a compound (4) in an anhydrous organic solvent to obtain a compound (5) in which the nitrogen atom at the 3-position is made into a quaternary salt. The molar ratio of the compound (4) to the compound (3) ranges from 5 to 100, preferably 20 to 50. Preferred examples of the reaction solvent include benzene, toluene, chloroform, dichloromethane, tetrahydrofuran, N,N-dimethylformamide and the like, with benzene and N,N-dimethylformamide being particularly preferred. The reaction may be effected at a temperature of preferably from −20° to +50° C., more preferably from 20° to 30° C. within 24 hours. After completion of the reaction, the reaction mixture is subjected to usual after-treatments and, if necessary, the thus obtained compound (5) is purified by means of silica gel column chromatography, Sephadex gel filtration, crystallization and the like.

In the step 3, protective groups $R^3$, $R^4$ and $R^5$ of the compound (5) are eliminated by deprotection to obtain the compound (I) of the present invention. The deprotection reaction for the elimination of the groups $R^3$, $R^4$ and $R^5$ may be carried out by usually used means in any optional order.

When $R^3$ is a trityl group, a formyl group or the like, $R^4$ is a trityl group, a tetrahydropyranyl group or the like and $R^5$ is p-methoxybenzyl group, diphenylmethyl group or the like, these groups can be deprotected under an acidic condition. In this instance, the compound (5) may be treated with a weak acid such as trifluoroacetic acid, formic acid or the like or a strong acid such as hydrochloric acid or the like. In the former case, the compound (5) is added to a weak acid which is used in an amount suitable for solvent use and allowed to react at 0° C. to room temperature for 1 to 2 hours. In the latter case, the compound (5) is reacted with 2 to 10 molar equivalents of a strong acid in methanol at 0° C. to room temperature for 1 to 2 hours.

When $R^3$ is an allyloxycarbonyl group or the like, $R^4$ is a trityl group or the like and $R^5$ is a p-nitrobenzyl group, a benzyl group, an allyl group or the like, part or all of these groups are eliminated under a reducing condition. In this instance, the compound (5) may be subjected to catalytic reduction using various types of catalyst, such as palladium-carbon, tetrakistriphenylphosphine palladium or the like or with a matallic reducing agent such as zinc or the like. The amount of the catalyst or the metallic reducing agent varies depending on the reactivity of the protective group. The reaction completes generally within 24 hours. Also, when $R^3$ is a chloroacetyl group, the compound (5) may be reacted with 1 to 2 molar equivalent various types of thioamide at 0° C. to room temperature for 1 to 2 hours. The thus obtained compound (I) can be crystallized and precipitated from its aqueous solution by adjusting pH. The compound (I) can be isolated and purified by means of a chromatography using a nonionic macroporous resin such as Diaion HP-20 or a gel filtration using Sephadex or the like.

The cephalosporin derivatives represented by formula (I) according to the present invention can also be produced in accordance with a production process (B) which comprises steps (a) to (d), as diagrammatically shown below.

Production process (B)

Step a

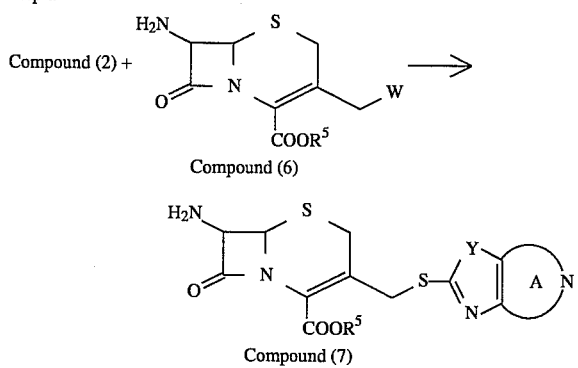

Compound (2) +

Compound (6)

Compound (7)

Step b

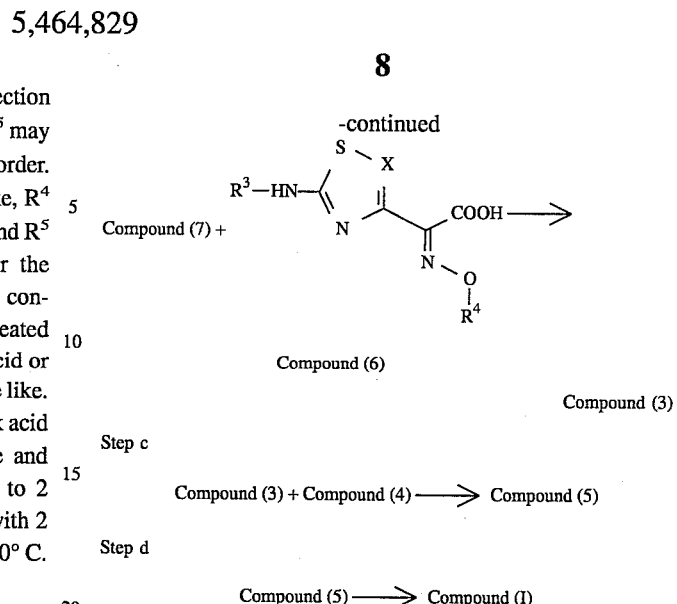

Compound (7) +

Compound (6)

Compound (3)

Step c

Compound (3) + Compound (4) ⟶ Compound (5)

Step d

Compound (5) ⟶ Compound (I)

In the reaction scheme of the above steps (a) to (d), each of $R^1$, $R^2$, $R^3$, $R^4$, $R^5$, X, Y and W has the same meaning as described in the aforementioned production process (A).

In the step (a) of the above production process (B), a compound (6) and a compound (2) are allowed to react each other in the same manner as in the step 1 of the production process (A) to obtain a compound (7).

The starting compound (6) can be synthesized in accordance with the known method as described in the references quoted above for the synthesis of the compound (1).

In the step (b), a compound (3) is obtained by effecting acylation of the 7-position amino group of a 7-aminocephem compound (7) using a compound (8) which is an aminothiazolyl acetate derivative or an aminothiadiazolyl acetate derivative. The acylation reaction may be effected by a usually used means in the field of peptide synthesis chemistry. For example, the compound (3) may be obtained by allowing the 7-aminocephem compound (7) to react with an aminothiazolyl or aminothiadiazolyl acetate derivative (8) or an active derivative thereof in the presence of various types of condensing agent. Examples of the condensing agent include dicyclohexylcarbodiimide, vilsmeier reagent, phosphorous oxychloride and the like. These agents may be selected optionally depending on the reactivity and the like of the compound (7) and aminothiazolyl acetic acid or aminothiadiazolyl acetic acid (8) or an active derivative thereof. The molar ratio of the compound (8) and the condensing agent to the compound (7) both ranges from 1.1 to 1.5. Preferred examples of the reaction solvent include dichloromethane, chloroform, N,N-dimethylformamide, tetrahydrofuran and the like. The reaction may be carried out at a temperature in the range of from −20° to +50° C., preferably from −20° to 0° C. for 1 to 2 hours. After completion of the reaction, the reaction mixture is subjected to usual after-treatments and, if necessary, the thus obtained compound (3) is purified by means of silica gel column chromatography and the like.

In the step (c), a compound (5) is obtained by allowing the compound (3) to react with a compound (4) in the same manner as in the step 2 of the aforementioned production process (A).

In the step (d), compound (I) is obtained by removing the protective group of compound (5) in the same manner as in the step 3 of the production process (A).

The cephalosporin derivatives represented by formula (I) according to the present invention can also be produced in accordance with a production process (C) which comprises steps i and ii, as diagrammatically shown below.

Production process (C)

Step i

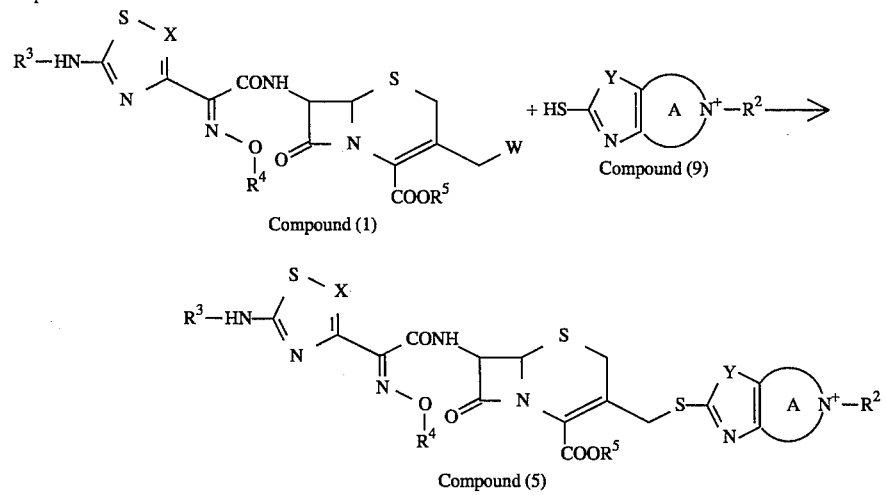

Step ii

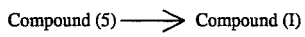

In the reaction scheme of the above steps i and ii, each of $R^1$, $R^2$, $R^3$, $R^4$, $R^5$, X, Y and W has the same meaning as described in the aforementioned production process (A).

In the step i of the above production process (C), a compound (1) and a compound (9) are allowed to react each other in the same manner as in the step 1 of the production process (A) to obtain a compound (5). The molar ratio of the compound (9) to the compound (1) ranges from 1.1 to 1.5.

In the step ii, the protective group of the compound (5) can be eliminated in the same manner as in the step 3 of the production process (A) to obtain the compound (I).

The thus obtained compound of formula (I) may be freeze-dried to be formulated into an antibacterial composition such as an injection upon use together with various pharmaceutically acceptable carriers such as fillers, binders and the like. The compound can be contained in the composition in an amount of 0.5 to 2 g, preferably 0.5 g, 1 g and 2 g per dosage form.

The cephalosporin derivatives of the present invention represented by formula (I) show strong antibacterial activities upon various pathogenic bacteria. The advantageous properties of typical examples of the compounds of the present invention are demonstrated in the following Test Example.

TEST EXAMPLE

Antibacterial activities of the following typical compounds A through E of the present invention represented by formula (I) upon various bacteria were determined by measuring the minimum inhibitory concentrations (MIC) in accordance with the known serial dilution technique. MIC was measured by inoculating $10^6$ CFU/ml of each test strain on a Sensitivity Plate Medium N (Nissui Pharmaceutical Co., Ltd.), incubating the plates at 35° C. for 18 to 20 hours and then evaluating the results.

Test Compounds:

A: 7-{(Z)-2-(2-aminothiazol-4-yl)-2-methoxyiminoacetamido}-3-(5-methylthiazolo[4,5-c]pyridinium-2-yl)thiomethyl-3-cephem-4-carboxylate
B: 7-{(Z)-2-(2-aminothiazol-4-yl)-2-methoxyiminoacetamido}-3-(4-methylthiazolo[4,5-b]pyridinium-2-yl)thiomethyl- 3-cephem-4-carboxylate
C: 7-{(Z)-2-(2-aminothiazol-4-yl)-2-carboxymethoxyiminoacetamido}-3-(5-methylthiazolo[4,5-c]pyridinium-2-yl)thiomethyl-3-cephem-4-carboxylate
D: 7-{(Z)-2-(2-aminothiazol-4-yl)-2-(1-carboxy-1-methylethoxyimino)acetamido}-3-(5-methylthiazolo[4,5-c]pyridinium-2-yl)thiomethyl-3-cephem-4-carboxylate
E: 7-[(Z)-2-(2-aminothiazol-4-yl)-2-{(S)-1-carboxyethoxyimino}acetamido]-3-(5-methylthiazolo[4,5-c]pyridinium-2-yl)thiomethyl-3-cephem-4-carboxylate Measured values of the minimum inhibitory concentration (μg/ml) of these compounds A to E are shown in Table 1.

TABLE 1

| | Minimum Inhibitory Concentration (μg/ml) of the compounds: | | | | |
|---|---|---|---|---|---|
| Test strain | A | B | C | D | E |
| S. aureus 209P JC-1 | 0.20 | 0.20 | 3.13 | 3.13 | 1.56 |
| S. epidermidis ATCC14990 | 0.20 | 0.20 | 3.13 | 3.13 | 1.56 |
| E. hirae ATCC8043 | 1.56 | 50 | 100 | >100 | >100 |
| E. coli NIHJ JC-2 | 0.05 | 0.10 | 0.05 | 0.20 | 0.20 |
| K. pneumoniae PCI602 | 0.05 | 0.05 | <0.025 | 0.20 | 0.05 |
| P. vulgaris GN76 | 0.39 | 0.20 | <0.025 | 0.10 | <0.025 |
| M. morganii | <0.025 | 0.10 | <0.025 | 0.05 | 0.05 |

TABLE 1-continued

| Test strain | Minimum Inhibitory Concentration (μg/ml) of the compounds: | | | | |
|---|---|---|---|---|---|
| | A | B | C | D | E |
| 1510/S-1 | | | | | |
| C. freundii GN346/16 | 0.10 | 0.10 | 0.20 | 0.39 | 0.39 |
| E. cloacae G-0008 | 0.05 | 0.20 | 0.05 | 0.20 | 0.20 |
| S. marcescens No. 1 | 0.05 | 0.20 | <0.025 | 0.05 | 0.05 |
| P. aeruginosa E-2 | 50 | 25 | 12.5 | 3.13 | 1.56 |

As shown in Table 1, it can be found that the cephalosporin derivatives represented by formula (I) according to the present invention show strong antibacterial activities. Thus, the derivatives are expected to be useful as a drug for the treatment of infectious diseases caused by various pathogenic bacteria.

The following examples are provided to further illustrate the present invention, but are not to be construed to limit the scope of the invention.

EXAMPLE 1

(a) Preparation of p-methoxybenzyl 7-{(Z)-2-(2-tritylaminothiazol-4-yl)-2-methoxyiminoacetamido}-3-(thiazolo[4,5-c]pyridin-2-yl)thiomethyl-3-cephem-4-carboxylate Five hundred mg of p-methoxybenzyl 7-{(Z)-2-(2-tritylaminothiazol-4-yl)-2-methoxyiminoacetamido}-3-chloromethyl-3-cephem-4-carboxylate was dissolved in 5 ml of acetone, 98 mg of sodium iodide was added thereto, and the resulting mixture was allowed to react at room temperature for 1 hour. After distilling off the solvent under a reduced pressure, 5 ml of N,N-dimethylformamide was added to the resulting residue to dissolve the residue therein and 116 mg of 2-mercaptothiazolo[4,5-c]pyridine was further added thereto. The resulting mixture was allowed to react at room temperature for 3.5 hours. To the reaction mixture were added 50 ml of ethyl acetate and 50 ml of 20% sodium chloride aqueous solution to separate an organic layer. The organic layer thus separated was washed with 20% sodium chloride aqueous solution and then dried over anhydrous magnesium sulfate. After distilling off the solvent under a reduced pressure, the resulting residue was purified by a column chromatography (70 g silica gel, toluene:ethyl acetate=2:1) to obtain 443 mg of the title compound in a yield of 76%.

NMR (CDCl$_3$) δ, 3.62 (1H, d, J=18 Hz), 3.75 (1H, d, J=18 Hz), 3.79 (3H, s), 4.05 (3H, s), 4.27 (1H, d, J=13 Hz), 4.79 (1H, d, J=13 Hz), 5.01 (1H, d, J=5 Hz), 5.27 (2H, s), 5.91 (1H, dd, J=5 Hz, 9 Hz), 6.72 (1H, s), 6.80 (1H, d, J=9 Hz), 6.88 (2H, d, J=9 Hz), 7.00 (1H, s), 7.1–7.30 (15H, m), 7.36 (2H, d, J=9 Hz), 7.70 (1H, d, J=6 Hz), 8.45 (1H, d, J=6 Hz), 9.09 (1H, s)

(b) Preparation of 7-{(Z)-2-(2-aminothiazol-4-yl)-2-methoxyiminoacetamido}- 3-(5-methylthiazolo[4,5-c]pyridinium-2-yl)thiomethyl-3-cephem-4-carboxylate A 443 mg portion of p-methoxybenzyl 7-{(Z)-2-(2-tritylaminothiazol- 4-yl)-2-methoxyiminoacetamido}-3-(thiazolo[4,5-c]pyridine-2-yl)thiomethyl-3-cephem-4-carboxylate was dissolved in 4 ml of benzene and 3.0 ml of methyl iodide was added thereto to carry out the reaction at room temperature for 26 hours. After distilling off the solvent under a reduced pressure, 2.2 ml of anisole was added to the resulting residue and cooled on an ice bath. To this was added 4.4 ml of trifluoro acetate to carry out the reaction at the same temperature for 1 hour. Thereafter, the resulting reaction mixture was added dropwise to 22 ml of diisopropyl ether. The thus purified precipitate was collected, dried and then suspended in 3 ml of distilled water, and the suspension was adjusted to pH 7 with a saturated sodium hydrogencarbonate aqueous solution. The resulting suspension was charged on a column packed with 40 ml of Diaion HP-20 resin (Mitsubishi Kasei Corporation). The column was washed with water and then, elution was carried out using 5% acetone solution and 10% acetone solution in this order. After the fraction containing the desired compound was concentrated under reduced pressure, the residue was dissolved in water and freeze-dried to obtain 179 mg of the title compound in a yield of 65%.

NMR (D$_2$O) δ, 3.50 (1H, d, J=18 Hz), 3.90 (1H, d, J=18 Hz), 4.03 (3H, s), 4.12 (1H, d, J=13 Hz), 4.52 (3H, s), 5.07 (1H, d, J=13 Hz), 5.16 (1H, d, J=5 Hz), 5.80 (1H, d, J=5 Hz), 7.03 (1H, s), 8.49 (1H, d, J=6 Hz), 8.55 (1H, d, J=6 Hz), 9.30 (1H, s)

EXAMPLE 2

(a) Preparation of p-methoxybenzyl 7-{(Z)-2-(2-tritylaminothiazol- 4-yl)-2-methoxyiminoacetamido}-3-(thiazolo[4,5-b]pyridin- 2-yl)thiomethyl-3-cephem-4-carboxylate Using 111 mg of 2-mercaptothiazolo[4,5-b]pyridine in place of 2-mercaptothiazolo[4,5-c]pyridine and 477 mg of p-methoxybenzyl 7-{(Z)-2-(2-tritylaminothiazol-4-yl)-2-methoxyiminoacetamido}- 3-chloromethyl-3-cephem-4-carboxylate, the reaction and purification were carried out in the same manner as in Example 1(a) to obtain 345 mg of the title compound in a yield of 62%.

NMR (CDCl$_3$) δ, 3.71 (1H, d, J=18 Hz), 3.80 (1H, d, J=18 Hz), 3.90 (3H, s), 4.06 (3H, s), 4.33 (1H, d, J=13 Hz), 4.86 (1H, s, J=13 Hz), 5.01 (1H, d, J=5 Hz), 5.26 (1H, d, J=6 Hz), 5.30 (1H, d, J=6 Hz), 5.90 (1H, dd, J=5 Hz, 9 Hz), 6.72 (1H, s), 6.79 (1H, d, J=9 Hz), 6.89 (2H, d, J=9 Hz), 7.03 (1H, s), 7.15–7.35 (16H, m), 7.37 (2H, d, J= 9 Hz), 8.10 (1H, d, J=6 Hz), 8.61 (1H, d, J=6 Hz), (b) Preparation of 7-{(Z)-2-(2-aminothiazol-4-yl)-2-methoxyiminoacetamido}- 3-(4-methylthiazolo[4,5-b]pyridinium-2-yl)thiomethyl-3-cephem-4-carboxylate Using 345 mg of p-methoxybenzyl 7-{(Z)-2-(2-tritylaminothiazol- 4-yl)-2-methoxyiminoacetamido}-3-(thiazolo[4,5-b]pyridine- 2-yl)thiomethyl-3-cephem-4-carboxylate as a starting material, the reaction and purification were carried out in the same manner as in Example 1(b) to obtain 64 mg of the title compound in a yield of 46%.

NMR (D$_2$O) δ, 3.50 (1H, d, J=18 Hz), 3.85 (1H, d, J=18 Hz), 3.96 (3H, s), 4.24 (1H, d, J=13 Hz), 4.53 (3H, s), 4.99 (1H, d, J=13 Hz), 5.15 (1H, d, J=5 Hz), 5.77 (1H, d, J=5 Hz), 6.99 (1H, s), 7.75 (1H, t, J=6 Hz), 8.68 (1H, d, J=6 Hz), 8.86 (1H, d, J=6 Hz)

EXAMPLE 3

(a) Preparation of p-methoxybenzyl 7-{(Z)-2-(2-tritylaminothiazol- 4-yl)-2-diphenylmethoxycarbonylmethoxyiminoacetamido}- 3-(thiazolo[4,5-c]pyridin-2-yl)thiomethyl-3-cephem-4-carboxylate Using 402 mg of p-methoxybenzyl 7-{(Z)-2-(2-tritylaminothiazol- 4-yl)-2-diphenylmethoxycarbonylmethoxyiminoacetamido}- 3-chloromethyl-3-cephem-4-carboxylate in place of p-methoxybenzyl 7-{(Z)-2-(2-tritylaminothiazol-4-yl)- 2-methoxyiminoacetamido}-3-chloromethyl-3-cephem-4-carboxylate and 74 mg of 2-mercaptothiazolo[4,5-c]pyridine, the reaction and purification were carried out in the same manner as in Example 1(a) to obtain 356 mg of the title compound in a yield of 78%.

NMR (CDCl$_3$) δ, 3.37 (1H, d, J=18 Hz), 3.61 (1H, d, J=18 Hz), 3.79 (3H, s), 4.22 (1H, d, J=13 Hz), 4.55 (1H, d, J=13 Hz), 4.94 (1H, d, J=5 Hz), 4.97 (1H, d, J=13 Hz), 5.00 (1H, d, J=13 Hz), 5.26 (1H, d, J=12 Hz), 5.30 (1H, d, J=12 Hz), 5.87 (1H, dd, J=5 Hz, 9 Hz), 6.77 (1H, s), 6.87 (2H, d, J=9 Hz), 6.96 (1H, s), 7.01 (1H, s), 7.15– 7.45 (27H, m), 7.71 (1H, d, J=6 Hz), 7.98 (1H, d, J=9 Hz), 8.46 (1H, d, J=6 Hz), 9.10 (1H, s)

(b) Preparation of 7-{(Z)-2-(2-aminothiazol-4-yl)-2-carboxymethoxyiminoacetamido}- 3-(5-methylthiazolo[4,5-c]pyridinium-2-yl)thiomethyl-3-cephem-4-carboxylate Using 356 mg of p-methoxybenzyl 7-{(Z)-2-(2-tritylaminothiazol- 4-yl)-2-diphenylmethoxycarbonylmethoxyiminoacetamido}- 3-(thiazolo[4,5-c]pyridin-2-yl)thiomethyl-3-cephem-4-carboxylate as a starting material, the reaction and purification were carried out in the same manner as in Example 1(b) to obtain 128 mg of the title compound as its sodium salt in a yield of 64%.

NMR (D$_2$O) δ, 3.47 (1H, d, J=18 Hz), 3.85 (1H, d, J=18 Hz), 4.02 (1H, d, J=13 Hz), 4.48 (3H, s), 4.56 (2H, s), 5.01 (1H, d, J=13 Hz), 5.12 (1H, d, J=5 Hz), 5.77 (1H, d, J=5 Hz), 7.01 (1H, s), 8.45 (1H, d, J=6 Hz), 8.51 (1H, d, J=6 Hz), 9.27 (1H, s)

EXAMPLE 4

(a) Preparation of p-methoxybenzyl 7-{(Z)-2-(2-tritylaminothiazol- 4-yl)-2-(1-tert-butoxycarbonyl-1-methylethoxyimino)acetamido}- 3-(thiazolo[4,5-c]pyridin-2-yl)thiomethyl-3-cephem-4-carboxylate Using 369 mg of p-methoxybenzyl 7-{(Z)-2-(2-tritylaminothiazol- 4-yl)-2-(1-tert-butoxycarbonyl-1-methylethoxyimino)acetamido}- 3-chloromethyl-3-cephem-4-carboxylate in place of p-methoxybenzyl 7-{(Z)-2-(2-tritylaminothiazol-4-yl)- 2-methoxyiminoacetamido}-3-chloromethyl-3-cephem-4-carboxylate and 74 mg of 2-mercaptothiazolo[4,5-c]pyridine, the reaction and purification were carried out in the same manner as in Example 1(a) to obtain 331 mg of the title compound in a yield of 79%.

NMR (CDCl$_3$) δ, 1.39 (9H, s), 1.58 (3H, s), 1.61 (3H, s), 3.57 (1H, d, J=18 Hz), 3.74 (1H, d, J=18 Hz), 3.79 (3H, s), 4.28 (1H, d, J=13 Hz), 4.80 (1H, d, J=13 Hz), 5.00 (1H, d, J=5 Hz), 5.23 (1H, d, J=12 Hz), 5.30 (1H, d, J=12 Hz), 5.97 (1H, dd, J=5 Hz, 9 Hz), 6.72 (1H, s), 6.87 (2H, d, J=9 Hz), 7.15–7.40 (18H, m), 7.70 (1H, d, J=6 Hz), 8.15 (1H, d, J=9 Hz), 8.46 (1H, d, J= 6 Hz), 9.09 (1H, s)

(b) Preparation of 7-{(Z)-2-(2-aminothiazol-4-yl)-2-(1-carboxy- 1-methylethoxyimino)acetamido}-3-(5-methylthiazolo[4,5-c]pyridinium- 2-yl)thiomethyl-3-cephem-4-carboxylate Using 331 mg of p-methoxybenzyl 7-{(Z)-2-(2-tritylaminothiazol- 4-yl)-2-(1-tert-butoxycarbonyl-1-methylethoxyimino)acetamido}- 3-(thiazolo[4,5-c]pyridin-2-yl)thiomethyl-3-cephem-4-carboxylate as a starting material, the reaction and purification were carried out in the same manner as in Example 1(b) to obtain 138 mg of the title compound in the form of a sodium salt in a yield of 65%.

NMR (D$_2$O) δ, 1.48 (3H, s), 1.50 (3H, s), 3.48 (1H, d, J= 18 Hz), 3.85 (1H, d, J=18 Hz), 4.10 (1H, d, J=13 Hz), 4.48 (3H, s), 5.04 (1H, d, J=13 Hz), 5.13 (1H, d, J=5 Hz), 5.77 (1H, d, J=5 Hz), 6.96 (1H, s), 8.46 (1H, d, J=6 Hz), 8.51 (1H, d, J=6 Hz), 9.27 (1H, s)

EXAMPLE 5

(a) Preparation of p-methoxybenzyl 7-[(Z)-2-(2-tritylaminothiazol- 4-yl)-2-{(S)-1-diphenylmethoxycarbonylethoxyimino}acetamido]- 3-(thiazolo[4,5-c]pyridin-2-yl)thiomethyl-3-cephem-4-carboxylate Using 306 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate in place of p-methoxybenzyl 7-{(Z)-2-(2-tritylaminothiazol-4-yl)- 2-methoxyiminoacetamido}-3-chloromethyl-3-cephem-4-carboxylate and 56 mg of 2-mercaptothiazolo[4,5-c]pyridine, the reaction and purification were carried out in the same manner as in Example 1(a) to obtain 276 mg of the title compound in a yield of 80%.

NMR (CDCl$_3$) δ, 1.57 (3H, d, J=7 Hz), 3.49 (1H, d, J=18 Hz), 3.65 (1H, d, J=18 Hz), 3.79 (3H, s), 4.27 (1H, d, J=13 Hz), 4.84 (1H, d, J=13 Hz), 4.93 (1H, d, J=5 Hz), 5.16 (1H, q, J=7 Hz), 5.23 (1H, d, J=12 Hz), 5.31 (1H, d, J=12 Hz), 5.87 (1H, dd, J=5 Hz, 9 Hz), 6.73 (1H, s), 6.86 (1H, s), 6.90 (2H, d, J=9 Hz), 7.00 (1H, s), 7.15–7.30 (25H, m), 7.36 (2H, d, J=9 Hz), 7.70 (1H, d, J=6 Hz), 8.05 (1H, d, J=9 Hz), 8.45 (1H, d, J=6 Hz), 9.09 (1H, s)

(b) preparation of 7-[(Z)-2-(2-aminothiazol-4-yl)-2-{(S)-1-carboxyethoxyimino}acetamido]- 3-(5-methylthiazolo[4,5-c]pyridinium-2-yl)thiomethyl-3-cephem-4-carboxylate Using 276 mg of p-methoxybenzyl 7-[(Z)-2-(2-tritylaminothiazol- 4-yl)-2-{(S)-1-diphenylmethoxycarbonylethoxyimino}acetamido]- 3-(thiazolo[4,5-c]pyridin-2-yl)thiomethyl-3-cephem-4-carboxylate as a starting material, the reaction and purification were carried out in the same manner as in Example 1(b) to obtain 84 mg of the title compound in the form of a sodium salt in a yield of 53%.

NMR (D$_2$O) δ, 1.46 (3H, d, J=7 Hz), 3.48 (1H, d, J=18 Hz), 3.85 (1H, d, J=18 Hz), 4.12 (1H, d, J=13 Hz), 4.49 (3H, s), 4.65 (1H, q, J=7 Hz), 5.03 (1H, d, J=13 Hz), 5.14 (1H, d, J=5 Hz), 5.78 (1H, d, J=5 Hz), 6.99 (1H, s), 8.46 (1H, d, J=6 Hz), 8.52 (1H, d, J=6 Hz), 9.28 (1H, s)

EXAMPLE 6

Preparation of 7-{(Z)-2-(5-aminothiadiazol-3-yl)-2-methoxyiminoacetamido}- 3-(5-methylthiazolo[4,5-c]pyridinium-2-yl)thiomethyl-3-cephem-4-carboxylate A 141 mg portion of p-methoxybenzyl 7-{(Z)-2-(5-aminothiadiazol- 3-yl)-2-methoxyiminoacetamido}-3-chloromethyl-3-cephem-4-carboxylate was dissolved in 2 ml of N,N-dimethylformamide and 47 mg of sodium iodide and 70 mg of 2-mercapto-5-methylthiazolo[4,5-c]pyridinium chloride were added thereto to allow the mixture to react at room temperature for 3 hours. To the reaction mixture were added 50 ml of ethyl acetate and 50 ml of a 20% sodium chloride aqueous solution. The precipitate thus formed was collected by filtration and 1 ml of anisole was added thereto. After cooling on an ice bath, 2 ml of trifluoroacetate was added to the solution followed by reaction at the same temperature for 1 hour. The resulting reaction mixture was added dropwise to 10 ml of diisopropyl ether, the precipitate thus formed was collected by filtration, dried and suspended in 3 ml of distilled water. The resulting solution was adjusted to pH 7 with a saturated sodium hydrogencarbonate aqueous solution and treated with 15 ml of HP-20 resin for purification. The resulting solution was freeze-dried to obtain 46 mg of the title compound in a yield of 26%.

NMR (D$_2$O) δ, 3.46 (1H, d, J=18 Hz), 3.88 (1H, d, J=18 Hz), 4.07 (1H, d, J=14 Hz), 4.08 (3H, s), 4.49 (3H, s), 5.07 (1H, d, J=14 Hz), 5.12 (1H, d, J=5 Hz), 5.80 (1H, d, J=5 Hz), 8.47 (1H, d, J=6 Hz)

EXAMPLE 7

Preparation of 7-{(Z)-2-(5-aminothiadiazol-3-yl)-2-(1-carboxy- 1-methylethoxyimino)acetamido}-3-(5-methylthiazolo[4,5-c]pyridinium- 2-yl)thiomethyl-3-cephem-4-carboxylate Using 204 mg of p-methoxybenzyl 7-{(Z)-2-(5-aminothiadiazol- 3-yl)-2-(1-tert-butoxycarbonyl-1-methylethoxyimino)acetamido}-3-chloromethyl- 3-cephem-4-carboxylate in place of p-methoxybenzyl 7-{(Z)-2-(2-tritylaminothiazol- 4-yl)-2-methoxyiminoacetamido}-3-chloromethyl-3-cephem-4-carboxylate and 57 mg of 2-mercaptothiazolo[4,5-c]pyridine, the reaction and purification were carried out in the same manner as in Example 1(a) and (b) to obtain 90 mg of the title compound in the form of a sodium salt in a yield of 45%.

NMR (D$_2$O) δ, 1.48 (6H, s), 3.43 (1H, d, J=18 Hz), 3.82 (1H, d, J=18 Hz), 4.07 (1H, d, J=14 Hz), 4.43 (3H, s), 4.83 (1H, d, J=14 Hz), 5.08 (1H, d, J=5 Hz), 5.71 (1H, d, J=5 Hz), 8.40 (1H, d, J=6 Hz), 8.47 (1H, d, J=6 Hz), 9.31 (1H, s)

EXAMPLE 8

(a) Preparation of p-methoxybenzyl 7-{(Z)-2-(2-tritylaminothiazol- 4-yl)-2-diphenylmethoxycarbonylmethoxyiminoacetamido}-3-(thiazolo[4,5-b]pyridin-2-yl)thiomethyl- 3-cephem-4-carboxylate Using 301 mg of p-methoxybenzyl 7-{(Z)-2-(2-tritylaminothiazol- 4-yl)-2-diphenylmethoxycarbonylmethoxyiminoacetamido}-3-chloromethyl-3-cephem-4-carboxylate and 60 mg of 2-mercaptothiazolo[4,5-b]pyridine in place of p-methoxybenzyl 7-{(Z)-2-(2-tritylaminothiazol-4-yl)-2-methoxyiminoacetamido}-3-chloromethyl-3-cephem-4-carboxylate and 2-mercaptothiazolo[4,5-c]pyridine, respectively, the reaction and purification were carried out in the same manner as in Example 1(a) to obtain 242 mg of the title compound in a yield of 71%.

NMR (CDCl$_3$) δ, 3.48 (1H, d, J=18 Hz), 3.66 (1H, d, J=18 Hz), 3.80 (3H, s), 4.29 (1H, d, J=13 Hz), 4.85–5.05 (4H, m), 5.28 (1H, d, J=12 Hz), 5.35 (1H, d, J=12 Hz), 5.87 (1H, dd, J=5 Hz, 9 Hz), 6.76 (1H, s), 6.88 (2H, d, J=9 Hz), 6.95 (1H, s), 7.00 (1H, s), 7.15–7.45 (26H, m), 7.96 (1H, d, J=9 Hz), 8.11 (1H, d, J=7 Hz), 8.62 (1H, d, J=7 Hz)

(b) Preparation of 7-{(Z)-2-(2-aminothiazol-4-yl)-2-carboxymethoxyiminoacetamide}- 3-(4-methylthiazolo[4,5-b]pyridinium-2-yl)thiomethyl-3-cephem-4-carboxylate Using 242 mg of p-methoxybenzyl 7-{(Z)-2-(2-tritylaminothiazol- 4-yl)-2-diphenylmethoxycarbonylmethoxyiminoacetamido)-3-(thiazolo[4,5-b]pyridin-2-yl)thiomethyl- 3-cephem-4-carboxylate as a starting material, the reaction and purification were carried out in the same manner as in Example 1(b) to obtain 33 mg of the title compound in the form of a sodium salt in a yield of 28%.

NMR (D$_2$O) δ, 3.51 (1H, d, J=18 Hz), 3.85 (1H, d, J=18 Hz), 4.30 (1H, d, J=13 Hz), 4.53 (3H, s), 4.59 (2H, s), 4.95 (1H, d, J=13 Hz), 5.19 (1H, d, J=5 Hz), 5.78 (1H, d, J=5 Hz), 6.94 (1H, s), 7.76 (1H, t, J=7 Hz), 8.69 (1H, d, J=7 Hz), 8.88 (1H, d, J=7 Hz)

EXAMPLE 9

Preparation of p-methoxybenzyl 7-{(Z)-2-(2-tritylaminothiazol- 4-yl)-2-(1-tert-butoxycarbonyl-1-methylethoxyimino)acetamido}- 3-(thiazolo[4,5-b]pyridin-2-yl)thiomethyl-3-cephem-4-carboxylate Using 276 mg of p-methoxybenzyl 7-{(Z)-2-(2-tritylaminothiazol- 4-yl)-2-(1-tert-butoxycarbonyl-1-methylethoxyimino)acetamido}- 3-chloromethyl-3-cephem-4-carboxylate and 60 mg of 2-mercaptothiazolo[4,5-b]pyridine in place of p-methoxybenzyl 7-{(Z)-2-(2-tritylaminothiazol-4-yl)- 2-methoxyiminoacetamido}-3-chloromethyl-3-cephem-4-carboxylate and 2-mercaptothiazolo[4,5-c]pyridine, respectively, the reaction and purification were carried out in the same manner as in Example 1(a) to obtain 191 mg of the title compound in a yield of 61%.

NMR (CDCl$_3$) δ, 1.40 (9H, s), 1.58 (3H, s), 1.62 (3H, s), 3.65 (1H, d, J=18 Hz), 3.76 (1H, d, J=18 Hz), 3.80 (3H, s), 4.35 (1H, d, J=13 Hz), 4.89 (1H, d, J=13 Hz), 5.00 (1H, d, J=5 Hz), 5.25 (1H, d, J=12 Hz), 5.35 (1H, d, J= 12 Hz), 5.97 (1H, dd, J=5 Hz, 9 Hz), 6.70 (1H, s), 6.84–6.94 (3H, m), 7.20–7.46 (16H, m), 8.10 (1H, d, J=7 Hz), 8.18 (1H, d, J=9 Hz), 8.61 (1H, d, J=7 Hz)

(b) Preparation of 7-{(Z)-2-(2-aminothiazol-4-yl)-2-(1-carboxy- 1-methylethoxyimino)acetamido}-3-(4-methylthiazolo[4,5-b]pyridinium- 2-yl)thiomethyl-3-cephem-4-carboxylate Using 191 mg of p-methoxybenzyl 7-{(Z)-2-(2-tritylaminothiazol- 4-yl)-2-(1-tert-butoxycarbonyl-1-methylethoxyimino)acetamido}- 3-(thiazolo[4,5-b]pyridin-2-yl)thiomethyl-3-cephem-4-carboxylate as a starting material, the reaction and purification were carried out in the same manner as in Example 1(b) to obtain 14 mg of the title compound in the form of a sodium salt in a yield of 11%.

NMR (D$_2$O) δ, 1.54 (3H, s), 1.56 (3H, s), 3.36 (1H, d, J=18 Hz), 3.90 (1H, d, J=18 Hz), 4.31 (1H, d, J=13 Hz), 4.58 (3H, s), 5.03 (1H, d, J=13 Hz), 5.21 (1H, d, J=5 Hz), 5.83 (1H, d, J= 5 Hz), 7.02 (1H, s), 7.80 (1H, t, J=7 Hz), 8.72 (1H, d, J=7 Hz), 8.92 (1H, d, J= 7 Hz)

EXAMPLE 10

Preparation of p-methoxybenzyl 7-[(Z)-2-(2-tritylaminothiazol- 4-yl)-2-{(S)-1-diphenylmethoxycarbonylethoxyimino}acetamido]- 3-(thiazolo[4,5-b]pyridin-2-yl)thiomethyl-3-cephem-4-carboxylate Using 305 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate and 60 mg of 2-mercaptothiazolo[4,5-b]pyridine in place of p-methoxybenzyl 7-{(Z)-2-(2-tritylaminothiazol-4-yl)-2-methoxyiminoacetamido}- 3-chloromethyl-3-cephem-4-carboxylate and 2-mercaptothiazolo[4,5-c]pyridine, respectively, the reaction and purification were carried out in the same manner as in Example 1(a) to obtain 215 mg of the title compound in a yield of 62%.

NMR (CDCl$_3$) δ, 1.60 (3H, d, J=7 Hz), 3.58 (1H, d, J=18 Hz), 3.69 (1H, d, J=18 Hz), 3.78 (3H, s), 4.33 (1H, d, J=13 Hz), 4.90 (1H, J=13 Hz), 4.92 (1H, d, J=5 Hz), 5.16 (1H, q, J=7 Hz), 5.25 (1H, d, J=12 Hz), 5.35 (1H, d, J=12 Hz), 5.88 (1H, dd, J=5 Hz, 9 Hz), 6.71 (1H, s), 6.86 (2H, d, J=9 Hz), 6.90 (1H, s), 6.99 (1H, s), 7.23–7.55 (28H, m), 8.00 (1H, d, J=9 Hz), 8.08 (1H, d, J=7 Hz), 8.61 (1H, d, J=7 Hz)

(b) Preparation of 7-[(Z)-2-(2-aminothiazol-4-yl)-2-{(S)-1-carboxymethoxyimino} acetamido]-3-(4-methylthiazolo-[4,5-b]pyridinium-2-yl)thiomethyl-3-cephem-4-carboxylate Using 215 mg of p-methoxybenzyl 7-[(Z)-2-(2-tritylaminothiazol- 4-yl)-2-{(S)-1-diphenylmethoxycarbonylethoxyimino}acetamido]-

3-(thiazolo[4,5-b]pyridin-2-yl)thiomethyl-3-cephem-4-carboxylate as a starting material, the reaction and purification were carried out in the same manner as in Example 1(b) to obtain 31 mg of the title compound in the form of a sodium salt in a yield of 72%.

NMR (D$_2$O) δ, 1.45 (3H, d, J=7 Hz), 3.53 (1H, d, J=18 Hz), 3.85 (1H, d, J=18 Hz), 4.30 (1H, d, J= 13 Hz), 4.55 (3H, s), 4.65 (1H, q, J=7 Hz), 4.99 (1H, d, J=13 Hz), 5.19 (1H, d, J= 5 Hz), 5.81 (1H, d, J=5 Hz), 6.98 (1H, s), 7.77 (1H, t, J=7 Hz), 8.70 (1H, d, J=7 Hz), 8.89 (1H, d, J=7 Hz)

EXAMPLE 11

(a) Preparation of p-methoxybenzyl 7-{(Z)-2-(2-tritylaminothiazol- 4-yl)-2-methoxyiminoacetamido]-3-(thiazolo[5,4-c]pyridin-2-yl)thiomethyl-3-cephem-4-carboxylate Using 60 mg of 2-mercaptothiazolo[5,4-c]pyridine in place of 2-mercaptothiazolo[4,5-c]pyridine and 238 mg of p-methoxybenzyl 7-{(Z)-2-(2-tritylaminothiazol-4-yl)-2-methoxyiminoacetamido}- 3-chloromethyl-3-cephem-4-carboxylate, the reaction and purification were carried out in the same manner as in Example 1(a) to obtain 186 mg of the title compound in a yield of 67%.

NMR (CDCl$_3$) δ, 3.59 (1H, d, J=18 Hz), 3.75 (1H, d, J=18 Hz), 3.80 (3H, s), 4.05 (3H, s), 4.26 (1H, d, J=13 Hz), 4.82 (1H, d, J=13 Hz), 5.02 (1H, d, J=5 Hz), 5.26 (1H, d, J=12 Hz), 5.30 (1H, d, J=12 Hz), 5.92 (1H, dd, J=5 Hz, 9 Hz), 6.72 (1H, s), 6.83 (1H, d, J=9 Hz), 6.88 (2H, d, J=9 Hz), 6.99 (1H, s), 7.10–7.55 (17H, m), 7.66 (1H, d, J=7 Hz), 8.57 (1H, d, J=7 Hz), 9.02 (1H, s)

(b) Preparation of 7-{(Z)-2-(2-aminothiazol-4-yl)-2-methoxyiminoacetamido}- 3-(5-methylthiazolo[5,4-c]pyridinium-2-yl)thiomethyl-3-cephem-4-carboxylate Using 186 mg of p-methoxybenzyl 7-{(Z)-2-(2-tritylaminothiazol- 4-yl)-2-methoxyiminoacetamido}-3-(thiazolo[5,4-c]pyridinium-2-yl)thiomethyl-3-cephem- 4-carboxylate as a starting material, the reaction and purification were carried out in the same manner as in Example 1(b) to obtain 43 mg of the title compound in a yield of 51%.

NMR (D$_2$O) δ, 3.50 (1H, d, J=18 Hz), 3.89 (1H, d, J=18 Hz), 4.01 (3H, s), 4.21 (1H, d, J=13 Hz), 4.44 (3H, s), 5.05 (1H, d, J=13 Hz), 5.18 (1H, d, J=5 Hz), 5.80 (1H, d, J=5 Hz), 7.03 (1H, s), 8.21 (1H, d, J=7 Hz), 8.65 (1H, d, J=7 Hz), 9.34 (1H, s)

EXAMPLE 12

(a) Preparation of p-methoxybenzyl 7-{(Z)-2-(2-tritylaminothiazol- 4-yl)-2-diphenylmethoxycarbonylmethoxyiminoacetamido}- 3-(thiazolo[5,4-c]pyridin-2-yl)thiomethyl-3-cephem-4-carboxylate Using 301 mg of p-methoxybenzyl 7-{(Z)-2-(2-tritylaminothiazol- 4-yl)-2-diphenylmethoxycarbonylmethoxyiminoacetamido}- 3-chloromethyl-3-cephem-4-carboxylate and 60 mg of 2-mercaptothiazolo[5,4-c]pyridine in place of p-methoxybenzyl 7-{(Z)-2-(2-tritylaminothiazol-4-yl)-2-methoxyiminoacetamido}-3-chloromethyl-3-cephem-4-carboxylate and 2-mercaptothiazolo[4,5-c]pyridine, respectively, the reaction and purification were carried out in the same manner as in Example 1(a) to obtain 256 mg of the title compound in a yield of 75%.

NMR (CDCl$_3$) δ, 3.34 (1H, d, J=18 Hz), 3.60 (1H, d, J=18 Hz), 3.78 (3H, s), 4.19 (1H, d, J=13 Hz), 4.85–5.05 (4H, m), 5.24 (1H, d, J=12 Hz), 5.33 (1H, d, J=12 Hz), 5.87 (1H, dd, J=5 Hz, 9 Hz), 6.76 (1H, s), 6.88 (2H, d, J=9 Hz), 6.96 (1H, s), 7.00 (1H, s), 7.15–7.50 (27H, m), 7.65 (1H, d, J=7 Hz), 7.98 (1H, d, J=9 Hz), 8.56 (1H, d, J=7 Hz), 9.02 (1H, s)

(b) Preparation of 7-{(Z)-2-(2-aminothiazol-4-yl)-2-carboxymethoxyiminoacetamido}- 3-(5-methylthiazolo[5,4-c]pyridinium-2-yl)thiomethyl-3-cephem-4-carboxylate Using 256 mg of p-methoxybenzyl 7-{(Z)-2-(2-tritylaminothiazol- 4-yl)-2-diphenylmethoxycarbonylmethoxyiminoacetamido}- 3-(thiazolo[5,4-c]pyridin-2-yl)thiomethyl-3-cephem-4-carboxylate as a starting material, the reaction and purification were carried out in the same manner as in Example 1(b) to obtain 59 mg of the title compound in the form of a sodium salt in a yield of 41%.

NMR (D$_2$O) δ, 3.50 (1H, d, J=18 Hz), 3.84 (1H, d, J=18 Hz), 4.25 (1H, d, J=13 Hz), 4.45 (3H, s), 4.59 (3H, s), 4.93 (1H, d, J=13 Hz), 5.19 (1H, d, J=5 Hz), 5.79 (1H, d, J=5 Hz), 6.95 (1H, s), 8.18 (1H, d, J=7 Hz), 8.64 (1H, d, J=7 Hz), 9.31 (1H, s)

EXAMPLE 13

(a) Preparation of p-methoxybenzyl 7-{(Z)-2-(2-tritylaminothiazol- 4-yl)-2-(1-tert-butoxycarbonyl-1-methylethoxyimino)acetamido}- 3-(thiazolo[5,4-c]pyridin-2-yl)thiomethyl-3-cephem-4-carboxylate Using 276 mg of p-methoxybenzyl 7-{(Z)-2-(2-tritylaminothiazol- 4-yl)-2-(1-tert-butoxycarbonyl-1-methylethoxyimino)acetamido}- 3-chloromethyl-3-cephem-4-carboxylate and 60 mg of 2-mercaptothiazolo[5,4-c]pyridine in place of p-methoxybenzyl 7-{(Z)-2-(2-tritylaminothiazol-4-yl)-2-methoxyimino-acetamido}-3-chloromethyl-3-cephem- 4-carboxylate and 2-mercaptothiazolo[4,5-c]pyridine, respectively, the reaction and purification were carried out in the same manner as in Example 1(a) to obtain 215 mg of the title compound in a yield of 68%.

NMR (CDCl$_3$) δ, 1.40 (9H, s), 1.58 (3H, s), 1.62 (3H, s), 3.54 (1H, d, J=18 Hz), 3.71 (1H, d, J=18 Hz), 3.79 (3H, s), 4.25 (1H, d, J=13 Hz), 4.84 (1H, d, J=13 Hz), 5.00 (1H, d, J=5 Hz), 5.24 (1H, d, J=12 Hz), 5.33 (1H, d, J= 12 Hz), 5.97 (1H, dd, J=5 Hz, 9 Hz), 6.72 (1H, s), 6.85–6.95 (3H, m), 7.10–7.40 (17H, m), 7.66 (1H, d, J=7 Hz), 8.02 (1H, d, J=9 Hz), 8.56 (1H, d, J=7 Hz), 9.01 (1H, s)

(b) Preparation of 7-{(Z)-2-(2-aminothiazol-4-yl)-2-(1-carboxy- 1-methylethoxyimino)acetamido}-3-(5-methylthiazolo[5,4-c]pyridinium- 2-yl)thiomethyl-3-cephem-4-carboxylate Using 215 mg of p-methoxybenzyl 7-{(Z)-2-(2-tritylaminothiazol- 4-yl)-2-(1-tert-butoxycarbonyl-1-methylethoxyimino)acetamido}- 3-(thiazolo[5,4-c]pyridin-2-yl)thiomethyl-3-cephem-4-carboxylate as a starting material, the reaction and purification were carried out in the same manner as in Example 1(b) to obtain 69 mg of the title compound in the form of a sodium salt in a yield of 51%.

NMR (D$_2$O) δ, 1.50 (3H, s), 1.52 (3H, s), 3.50 (1H, d, J=18 Hz), 3.85 (1H, d, J=18 Hz), 4.25 (1H, d, J=13 Hz), 4.43 (3H, s), 4.97 (1H, d, J=13 Hz), 5.18 (1H, d, J=5 Hz), 5.80 (1H, d, J=5 Hz), 6.93 (1H, s), 8.19 (1H, d, J=7 Hz), 8.64 (1H, d, J=7 Hz), 9.31 (1H, s)

EXAMPLE 14

(a) Preparation of p-methoxybenzyl 7-[(Z)-2-(2-tritylaminothiazol- 4-yl)-2-{(S)-1-diphenylmethoxycarbonylethoxyimino}acetamido]- 3-(thiazolo[5,4-c]pyridin-2-yl)thiomethyl-3-cephem-4-carboxylate Using 305 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate and 60 mg of 2-mercaptothiazolo[5,4-c]pyridine in place of p-methoxybenzyl 7-{(Z)-2-(2-tritylaminothiazol-4-yl)-2-methoxyiminoacetamido}- 3-chloromethyl-3-cephem-4-carboxylate and 2-mercaptothiazolo[4,5-c]pyridine, respectively, the reaction and purification were carried out in the same manner as in Example 1(a) to obtain 218 mg of the title compound in a yield of 63%.

NMR (CDCl$_3$) δ, 1.60 (1H, d, J=7 Hz), 3.47 (1H, d, J=18 Hz), 3.65 (1H, d, J=18 Hz), 3.79 (3H, s), 4.25 (1H, d, J=13 Hz), 4.88 (1H, d, J=13 Hz), 4.93 (1H, d, J=5 Hz), 5.18 (1H, q, J= 7 Hz), 5.23 (1H, d, J=12 Hz), 5.34 (1H, d, J=12 Hz), 5.87 (1H, dd, J=5 Hz, 9 Hz), 6.73 (1H, s), 6.80–6.95 (3H, m), 6.98 (1H, s), 7.10–7.40 (27H, m), 7.65 (1H, d, J=7 Hz), 8.05 (1H, d, J=9 Hz), 8.57 (1H, d, J=7 Hz), 9.01 (1H, s)

(b) Preparation of 7-[(Z)-2-(2-aminothiazol-4-yl)-2-{(S)-1-carboxyethoxyimino}acetamido]- 3-(5-methylthiazolo-[5,4-c]pyridinium-2-yl)thiomethyl-3-cephem-4-carboxylate Using 218 mg of p-methoxybenzyl 7-{(Z)-2-(2-tritylaminothiazol- 4-yl)-2-{(S)-diphenylmethoxycarbonylethoxyimino}acetamido]- 3-(thiazolo[5,4-c]pyridin-2-yl)thiomethyl-3-cephem-4-carboxylate as a starting material, the reaction and purification were carried out in the same manner as in Example 1(b) to obtain 62 mg of the title compound in the form of a sodium salt in a yield of 49%.

NMR (D$_2$O) δ, 1.47 (3H, d, J=7 Hz), 3.49 (1H, d, J=18 Hz), 3.84 (1H, d, J=18 Hz), 4.25 (1H, d, J= 13 Hz), 4.43 (3H, s), 4.68 (1H, q, J=7 Hz), 4.94 (1H, d, J=13 Hz), 5.19 (1H, d, J= 5 Hz), 5.79 (1H, d, J=5 Hz), 6.93 (1H, s), 8.18 (1H, d, J=7 Hz), 8.63 (1H, d, J=7 Hz), 9.31 (1H, s)

EXAMPLE 15

(a) Preparation of p-methoxybenzyl 7-{(Z)-2-(2-tritylaminothiazol- 4-yl)-2-methoxyiminoacetamido}-3-(4-methylthiazolo[5,4-b]pyridin- 2-yl)thiomethyl-3-cephem-4-carboxylate trifluoroacetate A 238 mg portion of p-methoxybenzyl 7-{(Z)-2-(2-tritylaminothiazol- 4-yl)-2-methoxyiminoacetamido}-3-chloromethyl-3-cephem-4-carboxylate was dissolved in 3 ml of acetone, 47 mg of sodium iodide was added thereto and the resulting mixture was allowed to react at room temperature for 1 hour. After the solvent was distilled off under a reduced pressure, 3 ml of N,N-dimethylformamide was added to dissolve the residue. A 107 mg portion of 2-mercapto-4-methylthiazolo[5,4-b]pyridinium trifluoroacetate was added thereto followed by reaction at room temperature for 3 hours. To the reaction mixture were added 50 ml of dichloromethane and 50 ml of a 20% sodium chloride aqueous solution for separation of an organic layer. The organic layer was washed with a 20% sodium chloride aqueous solution and a 5% sodium thiosulfate aqueous solution and dried over anhydrous magnesium sulfate. After the solvent was distilled off under a reduced pressure, the residue was subjected to gel column chromatography LH-20 (chloroform:methanol=1:1) for purification to obtain 227 mg of the title compound in a yield of 72%.

NMR (CDCl$_3$) δ, 3.52 (1H, d, J=18 Hz), 3.77 (1H, d, J=18 Hz), 3.80 (3H, s), 4.05 (3H, s), 4.27 (1H, d, J=13 Hz), 4.77 (3H, s), 4.86 (1H, d, J=13 Hz), 5.07 (1H, d, J=5 Hz), 5.21 (1H, d, J=12 Hz), 5.33 (1H, d, J=12 Hz), 5.90 (1H, dd, J=5 Hz, 9 Hz), 6.67 (1H, s), 6.82 (1H, d, J=9 Hz), 6.88 (2H, d, J=9 Hz), 7.05 (1H, s), 7.20–7.30 (15H, m), 7.36 (2H, d, J= 9 Hz), 8.97 (1H, dd, J=7 Hz, 9 Hz), 8.37 (1H, d, J=9 Hz), 9.74 (1H, d, J=7 Hz)

(b) Preparation of 7-{(Z)-2-(2-aminothiazol-4-yl)-2-methoxyimino}acetamido]- 3-(4-methylthiazolo[5,4-b]pyridinium-2-yl)thiomethyl-3-cephem-4-carboxylate Using 227 mg of p-methoxybenzyl 7-{(Z)-2-(2-tritylaminothiazol- 4-yl)-2-methoxyiminoacetamido]-3-(4-methylthiazolo[5,4-b]pyridinium- 2-yl)thiomethyl-3-cephem-4-carboxylate trifluoroacetate as a starting material, the reaction and purification were carried out in the same manner as in Example 1(b) to obtain 65 mg of the title compound in a yield of 52%.

NMR (D$_2$O) δ, 3.49 (1H, d, J=18 Hz), 3.89 (1H, d, J=18 Hz), 3.99 (3H, s), 4.14 (1H, d, J=13 Hz), 4.51 (3H, s), 5.02 (1H, d, J=13 Hz), 5.14 (1H, d, J=5 Hz), 5.77 (1H, d, J=5 Hz), 7.00 (1H, s), 8.02 (1H, dd, J=7 Hz, 9 Hz), 8.77 (2H, d, J=7 Hz)

EXAMPLE 16

(a) Preparation of p-methoxybenzyl 7-{(Z)-2-(2-tritylaminothiazol- 4-yl)-2-diphenylmethoxycarbonylmethoxyiminoacetamido}-3-( 4-methylthiazolo-[5,4-b]pyridinium-2-yl)-thiomethyl-3-cephem-4-carboxylate trifluoroacetate Using 301 mg of p-methoxybenzyl 7-{(Z)-2-(2-tritylaminothiazol- 4-yl)-2-diphenylmethoxycarbonylmethoxyiminoacetamido}- 3-chloromethyl-3-cephem-4-carboxylate in place of p-methoxybenzyl 7-{(Z)-2-(2-tritylaminothiazol-4-yl)- 2-methoxyiminoacetamido}-3-chloromethyl-3-cephem-4-carboxylate and 107 mg of 2-mercapto-4-methylthiazolo-[5,4-b]pyridinium trifluoroacetate, the reaction and purification were carried out in the same manner as in Example 15(a) to obtain 305 mg of the title compound in a yield of 80%.

NMR (CDCl$_3$) δ, 3.28 (1H, d, J=18 Hz), 3.64 (1H, d, J=18 Hz), 3.79 (3H, s), 4.16 (1H, d, J=13 Hz), 4.67 (3H, s), 4.85–5.05 (4H, m) 5.21 (1H, d, J=12 Hz), 5.36 (1H, d, J=12 Hz), 5.83 (1H, dd, J=5 Hz, 9 Hz), 6.76 (1H, s), 6.89 (2H, d, J=9 Hz), 6.95 (1H, s), 7.20–7.40 (28H, m), 7.91 (1H, dd, J=7 Hz, 9 Hz), 8.03 (1H, d, J=9 Hz), 8.30 (1H, d, J=9 Hz), 9.42 (1H, d, J=7 Hz)

(b) Preparation of 7-{(Z)-2-(2-aminothiazol-4-yl)-2-carboxymethoxyiminoacetamido}- 3-(4-methylthiazolo-[5,4-b]pyridinium-2-yl)thiomethyl-3-cephem-4-carboxylate Using 305 mg of p-methoxybenzyl 7-{(Z)-2-(2-tritylaminothiazol- 4-yl)-2-diphenylmethoxycarbonylmethoxyiminoacetamido}- 3-(4-methylthiazolo[5,4-b]pyridinium-2-yl)thiomethyl- 3-cephem-4-carboxylate trifluoroacetate, the reaction and purification were carried out in the same manner as in Example 1(b) to obtain 105 mg of the title compound in a yield of 68%.

NMR (D$_2$O) δ, 3.49 (1H, d, J=18 Hz), 3.86 (1H, d, J=18 Hz), 4.16 (1H, d, J=13 Hz), 4.50 (3H, s), 4.56 (2H, s), 4.99 (1H, d, J=13 Hz), 5.14 (1H, d, J=5 Hz), 5.79 (1H, d, J=5 Hz), 7.03 (1H, s), 8.01 (1H, t, J=9 Hz), 8.76 (2H, d, J=9 Hz)

EXAMPLE 17

(a) Preparation of p-methoxybenzyl 7-{(Z)-2-(2-tritylaminothiazol- 4-yl)-2-(1-tert-butoxycarbonyl-1-methylethoxyimino)acetamido}- 3-(4-methylthiazolo-[5,4-b]pyridinium-2-yl)thiomethyl-3-cephem-4-carboxylate trifluoroacetate Using 277 mg of p-methoxybenzyl 7-{(Z)-2-(2-tritylaminothiazol- 4-yl)-2-(1-tert-butoxycarbonyl-1-methylethoxyimino)acetamido}- 3-chloromethyl-3-cephem-4-carboxylate in place of p-methoxybenzyl 7-{(Z)-2-(2-tritylaminothiazol-4-yl)- 2-methoxyiminoacetamido}-3-chloromethyl-3-cephem-4-carboxylate and 107 mg of 2-mercapto-4-methylthiazolo-[5,4-b]pyridinium trifluoroacetate, the reaction and purification were carried out in the same manner as in Example 15(a) to obtain 327 mg of the title compound in a yield of 92%.

NMR (CDCl₃) δ, 1,41 (9H, s), 1.58 (3H, s), 1.62 (3H, s), 3.45 (1H, d, J=18 Hz), 3.76 (1H, d, J=18 Hz), 3.79 (3H, s), 4.22 (1H, d, J=13 Hz), 4.76 (3H, s), 4.91 (1H, d, J=13 Hz), 5.07 (1H, d, J=5 Hz), 5.20 (1H, d, J=12 Hz), 5.35 (1H, d, J=12 Hz), 5.94 (1H, dd, J=5 Hz, 9 Hz), 6.70 (1H, s), 6.80–6.90 (3H, m), 7.20–7.30 (15H, m), 7.36 (2H, d, J=9 Hz), 7.98 (1H, dd, J=7 Hz, 9 Hz), 8.17 (1H, d, J= 9 Hz), 8.36 (1H, d, 9 Hz), 9.45 (1H, d, J= 7 Hz)

(b) Preparation of 7-{(Z)-2-(2-aminothiazol-4-yl)-2-(1-carboxy- 1-methylethoxyimino)acetamido}-3-(4-methylthiazolo[5,4-b]pyridinium- 2-yl)thiomethyl-3-cephem-4-carboxylate Using 327 mg of p-methoxybenzyl 7-{(Z)-2-(2-tritylaminothiazol- 4-yl)-2-(1-tert-butoxycarbonyl-1-methylethoxyimino)acetamido}- 3-(4-methylthiazolo[5,4-b]pyridinium-2-yl)thiomethyl-3-cephem-4-carboxylate trifluoroacetate as a starting material, the reaction and purification were carried out in the same manner as in Example 1(b) to obtain 128 mg of the title compound in the form of a sodium salt in a yield of 69%.

NMR (D₂O) δ, 1.49 (3H, s), 1.50 (3H, s), 3.50 (1H, d, J=18 Hz), 3.87 (1H, d, J=18 Hz), 4.16 (1H, d, J=13 Hz), 4.51 (3H, s), 5.00 (1H, d, J=13 Hz), 5.15 (1H, d, J=5 Hz), 5.79 (1H, d, J=5 Hz), 6.98 (1H, s), 8.02 (1H, t, J=9 Hz), 8.77 (2H, d, J=9 Hz)

EXAMPLE 18

(a) Preparation of p-methoxybenzyl 7-[(Z)-2-(2-tritylaminothiazol- 4-yl)-2-{(S)-diphenylmethoxycarbonylethoxyimino}acetamido]- 3-(4-methylthiazolo-[5,4-b]pyridinium-2-yl)thiomethyl-3-cephem-4-carboxylate trifluoroacetate Using 306 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate in place of p-methoxybenzyl 7-{(Z)-2-(2-tritylaminothiazol-4-yl)-2-methoxyiminoacetamido}-3-chloromethyl-3-cephem-4-carboxylate and 107 mg of 2-mercapto-4-methylthiazolo-[5,4-b]pyridinium trifluoroacetate, the reaction and purification were carried out in the same manner as in Example 15(a) to obtain 329 mg of the title compound in a yield of 86%.

NMR (CDCl₃) δ, 1.60 (3H, d, J=7 Hz), 3.40 (1H, d, J=18 Hz), 3.70 (1H, d, J=18 Hz), 3.78 (3H, s), 4.18 (1H, d, J=13 Hz), 4.68 (3H, s), 5.01 (1H, d, J=5 Hz), 5.16 (1H, q, J=7 Hz), 5.19 (1H, d, J=12 Hz), 5.35 (1H, d, J=12 Hz), 5.85 (1H, dd, J=5 Hz, 9 Hz), 6.71 (1H, s), 6.87 (2H, d, J=9 Hz), 6.90 (1H, s), 6.98 (1H, s), 7.15–7.35 (25H, m), 7.36 (2H, d, J=9 Hz), 7.96 (1H, dd, J=7 Hz, 9 Hz), 8.02 (1H, d, J=9 Hz), 8,33 (1H, d, J= 9 Hz), 9.47 (1H, d, J=7 Hz)

(b) Preparation of 7-{(Z)-2-(2-aminothiazol-4-yl)-2-{(S)-1-carboxyethoxyimino} acetamido]-3-(4-methylthiazolo-[5,4-b]pyridinium- 2-yl)thiomethyl-3-cephem-4-carboxylate Using 329 mg of p-methoxybenzyl 7-[(Z)-2-(2-tritylaminothiazol- 4-yl)-2-{(S)-1-diphenylmethoxycarbonylethoxyimino}acetamido]- 3-(4-methylthiazolo[5,4-b]pyridinium-2-yl)thiomethyl-3-cephem-4-carboxylate trifluoroacetate as a starting material, the reaction and purification were carried out in the same manner as in Example 1(b) to obtain 108 mg of the title compound in the form of a sodium salt in a yield of 64%.

NMR (D₂O) δ, 1.45 (3H, d, J=7 Hz), 3.49 (1H, d, J=18 Hz), 3.86 (1H, d, J=18 Hz), 4.15 (1H, d, J= 13 Hz), 4.50 (3H, s), 4.65 (1H, q, J=7 Hz), 4.99 (1H, d, J=13 Hz), 5.14 (1H, t, J= 5 Hz), 5.79 (1H, d, J=5 Hz), 7.01 (1H, s), 8.01 (1H, dd, J=7 Hz, 9 Hz), 8.76 (1H, d, J=7 Hz), 8.76 (1H, d, J=9 Hz)

EXAMPLE 19

(a) Preparation of 7-{(Z)-2-(2-aminothiazol-4-yl)-2-methoxyiminoacetamido}- 3-(5-carboxymethylthiazolo-[4,5-c] pyridinium-2-yl)thiomethyl-3-cephem-4-carboxylate A 312 mg portion of p-methoxybenzyl 7-{(Z)-2-(2-tritylaminothiazol- 4-yl)-2-methoxyiminoacetamido}-3-(thiazolo[4,5-c]pyridin- 2-yl)thiomethyl-3-cephem-4-carboxylate was dissolved in 3 ml of benzene, 815 mg of tert-butyl iodoacetate was added thereto and the resulting mixture was allowed to react at room temperature for 51 hours. After the solvent was distilled off under a reduced pressure, the residue was dissolved in water and charged on a column packed with Sephadex LH-20 (Pharmacia). Elution was carried out with 50% methanol solution. Then, 1.5 ml of anisole was added to the fraction containing the desired compound followed by cooling on an ice bath. After further adding 3.0 ml of trifluoroacetate thereto, the resulting mixture was allowed to react at the same temperature for 30 minutes and then at room temperature for 3 hours. The reaction mixture was added dropwise to 15 ml of diisopropyl ether. The precipitate thus formed was collected by filtration, dried and suspended in 3 ml of distilled water. The resulting solution was adjusted to pH 7 with a saturated sodium hydrogencarbonate aqueous solution and treated with 30 ml of Diaion HP-20 resin for purification followed by freeze-drying to obtain 95 mg of the title compound in the form of a sodium salt in a yield of 44%.

NMR (D₂O) δ, 3.49 (1H, d, J=18 Hz), 3.86 (1H, d, J=18 Hz), 3.98 (1H, s), 4.15 (1H, d, J=13 Hz), 4.96 (1H, d, J=13 Hz), 5.14 (1H, d, J=5 Hz), 5.32 (2H, s), 5.78 (1H, d, J=5 Hz), 7.00 (1H, s), 8.51 (2H, s), 9.26 (1H, s)

EXAMPLE 20

(a) Preparation of p-methoxybenzyl 7-[(Z)-2-(2-tritylaminothiazol- 4-yl)-2-{(S)-diphenylmethoxycarbonylethoxyimino}acetamido]- 3-(5-methylthiazolo[4,5-c]pyridinium-2-yl)thiomethyl-3-cephem-4-carboxylate trifluoroacetate Using 306 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate and 112 mg of 5-ethyl-2-mercaptothiazolo[4,5-c]pyridinium trifluoroacetate in place of p-methoxybenzyl 7-{(Z)-2-(2-tritylaminothiazol- 4-yl)-2-methoxyiminoacetamido}-3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 322 mg of the title compound in a yield of 83%.

NMR (CDCl₃) δ, 1.60 (3H, d, J=7 Hz), 1.72 (3H, d, J=7 Hz), 3.42 (1H, d, J=18 Hz), 3.68 (1H, d, J= 18 Hz), 3.78 (3H, s), 4.22 (1H, d, J=13 Hz), 4.89 (1H, d, J=13 Hz), 4.90–5.05 (3H, m), 5.17 (1H, d, J=7 Hz), 5.23 (1H, d, J=13 Hz), 5.35 (1H, d, J=13 Hz), 5.87 (1H, dd, J=5 Hz, 9 Hz), 6.72 (1H, s), 6.87 (2H, d, J=9 Hz), 6.91 (1H, s), 6.98 (1H, br-s), 7.20–7.35 (20H, m), 7.36 (2H, d, J=9 Hz), 8.06 (1H, d, J=9 Hz), 8.69 (1H, d, J=7 Hz), 9.15 (1H, s), 9.33 (1H, d, J=7 Hz)

(b) Preparation of 7-{(Z)-2-(2-aminothiazol-4-yl)-2-{(S)-1-carboxyethoxyimino}acetamido]- 3-(5-ethylthiazolo[4,5-c] pyridinium-2-yl)thiomethyl-3-cephem-4-carboxylate Using 322 mg of p-methoxybenzyl 7-[(Z)-2-(2-tritylaminothiazol- 4-yl)-2-{(S)-1-diphenylmethoxycarbonylethoxyimino}acetamido]- 3-(5-ethylthiazolo[4,5-c]pyridinium-2-yl)thiomethyl- 3-cephem- 4-carboxylate trifluoroacetate as a starting material, the reaction and purification were carried out in the same manner as in Example 1(b) to obtain 112 mg of the title compound in the form of a sodium salt in a yield of 67%.

NMR (D$_2$O) δ, 1.45 (3H, d, J=7 Hz), 1.68 (3H, t, J=7 Hz), 3.47 (1H, d, J=18 Hz), 3.85 (1H, d, J= 18 Hz), 4.11 (1H, d, J=13 Hz), 4.64 (1H, q, J=7 Hz), 4.74 (2H, q, J=7 Hz), 5.04 (1H, d, J=13 Hz), 5.13 (1H, d, J=5 Hz), 5.79 (1H, d, J=5 Hz), 7.00 (1H, s), 8.48 (1H, d, J=7 Hz), 8.59 (1H, d, J=7 Hz), 9.35 (1H, s)

EXAMPLE 21

(a) Preparation of p-methoxybenzyl 7-{(Z)-2-(2-tritylaminothiazol- 4-yl)-2-(1-tert-butoxycarbonyl-1-methylethoxyimino)acetamido}- 3-(5-methylthiazolo-[4,5-c]pyridinium-2-yl)thiomethyl- 3-cephem-4-carboxylate trifluoroacetate Using 277 mg of p-methoxybenzyl 7-{(Z)-2-(2-tritylaminothiazol- 4-yl)-2-(1-tert-butoxycarbonyl-1-methylethoxyimino)acetamido}- 3-chloromethyl-3-cephem-4-carboxylate and 112 mg of 5-ethyl-2-mercaptothiazolo-[4,5-c]pyridinium trifluoroacetate in place of p-methoxybenzyl 7-{(Z)- 2-(2-tritylaminothiazol-4-yl)-2-methoxyiminoacetamido}- 3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 253 mg of the title compound in a yield of 70%.

NMR (CDCl$_3$) δ, 1.41 (9H, s), 1.58 (3H, s), 1.61 (3H, s), 1.72 (3H, d, J=7 Hz), 3.46 (1H, d, J=18 Hz), 3.76 (1H, d, J=18 Hz), 3.78 (3H, s), 4.21 (1H, d, J=13 Hz), 4.90 (1H, d, J=13 Hz), 4.95 (2H, q, J=7 Hz), 5.02 (1H, d, J=5 Hz), 5.23 (1H, d, J=12 Hz), 5.35 (1H, d, J=12 Hz), 5.96 (1H, dd, J=5 Hz, 9 Hz), 6.72 (1H, s), 6.87 (2H, d, J=9 Hz), 7.20– 7.35 (15H, m), 7.37 (2H, d, J=9 Hz), 8.18 (1H, d, J=9 Hz), 8.73 (1H, d, J=9 Hz), 9.12 (1H, s), 9.28 (1H, d, J=9 Hz)

(b) Preparation of 7-{(Z)-2-(2-aminothiazol-4-yl)-2-(1-carboxy- 1-methylethoxyimino)acetamido}-3-(5-ethylthiazolo-[4,5-c]pyridinium- 2-yl)thiomethyl-3-cephem-4-carboxylate Using 253 mg of p-methoxybenzyl 7-{(Z)-2-(2-tritylaminothiazol- 4-yl)-2-(1-tert-butoxycarbonyl-1-methylethoxyimino)acetamido}- 3-(5-ethylthiazolo[4,5-c]pyridinium-2-yl)thiomethyl-3-cephem-4-carboxylate trifluoroacetate as a starting material, the reaction and purification were carried out in the same manner as in Example 1(b) to obtain 92 mg of the title compound in the form of a sodium salt in a yield of 64%.

NMR (D$_2$O) δ, 1.48 (3H, s), 1.49 (3H, s), 1.69 (3H, t, J=7 Hz), 3.48 (1H, d, J=18 Hz), 3.85 (1H, d, J=18 Hz), 4.12 (1H, d, J=13 Hz), 4.74 (2H, q, J=7 Hz), 5.03 (1H, d, J=13 Hz), 5.13 (1H, d, J=5 Hz), 5.77 (1H, d, J=5 Hz), 6.96 (1H, s), 8.48 (1H, d, J=6 Hz), 8.60 (1H, d, J=6 Hz), 9.35 (1H, s)

EXAMPLE 22

(a) Preparation of p-methoxybenzyl 7-[(Z)-2-(2-tritylaminothiazol- 4-yl)-2-{(S)-1-diphenylmethoxycarbonylethoxyimino}acetamido]- 3-{5-(2-fluoroethyl)thiazolo-[4,5-c]pyridinium-2-yl)thiomethyl-3-cephem-4-carboxylate trifluoroacetate Using 306 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate and 118 mg of 5-(2-fluoroethyl)-2-mercaptothiazolo-[4,5-c]pyridinium trifluoroacetate in place of p-methoxybenzyl 7-{(Z)- 2-(2-tritylaminothiazol-4-yl)-2-methoxyiminoacetamido}-3- tritylaminothiazol-4-yl)-2-methoxyiminoacetamido}-3- chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 280 mg of the title compound in a yield of 71%.

NMR (CDCl$_3$) δ, 1.61 (3H, d, J=7 Hz), 3.43 (1H, d, J=18 Hz), 3.67 (1H, d, J=18 Hz), 3.78 (3H, s), 4.27 (1H, d, J=13 Hz), 4.85 (1H, d, J=13 Hz), 4.95 (1H, d, J=5 Hz), 4.98 (2H, dt, J= 4 Hz, 47 Hz), 5.10–5.45 (5H, m), 5.88 (1H, dd, J=5 Hz, 9 Hz), 6.72 (1H, s), 6.87 (2H, d, J=9 Hz), 6.90 (1H, s), 6.97 (1H, s), 7.20–7.35 (25H, m), 7.35 (2H, d, J=9 Hz), 8.03 (1H, d, J=9 Hz), 8.46 (1H, d, J=7 Hz), 9.11 (1H, d, J=7 Hz), 9.24 (1H, s)

(b) Preparation of 7-[(Z)-2-(2-aminothiazol-4-yl)-2-{(S)-1-carboxyethoxyimino}acetamido]- 3-{5-(2-fluoroethyl)thiazolo[4,5-c]pyridinium-2-yl}thiomethyl-3-cephem-4-carboxylate Using 280 mg of p-methoxybenzyl 7-[(Z)-2-(2-tritylaminothiazol- 4-yl)-2-{(S)-1-diphenylmethoxycarbonylethoxyimino}acetamido]- 3-{5-(2-fluoroethyl)thiazolo[4,5-c]pyridinium-2-yl)thiomethyl-3-cephem-4-carboxylate trifluoroacetate as a starting material, the reaction and purification were carried out in the same manner as in Example 1(b) to obtain 102 mg of the title compound in the form of a sodium salt in a yield of 69%.

NMR (D$_2$O) δ, 1.46 (1H, d, J=7 Hz), 3.48 (1H, d, J=18 Hz), 3.86 (1H, d, J=18 Hz), 4.12 (1H, d, J= 13 Hz), 4.65 (1H, q, J=7 Hz), 4.90–5.15 (6H, m), 5.79 (1H, d, J=5 Hz), 7.01 (1H, s), 8.53 (1H, d, J=7 Hz), 8.62 (1H, d, J=7 Hz), 9.38 (1H, s)

EXAMPLE 23

(a) Preparation of p-methoxybenzyl 7-{(Z)-2-(2-tritylaminothiazol- 4-yl)-2-(1-tert-butoxycarbonyl-1-methylethoxyimino)acetamido}- 3-{5-(2-fluoroethyl)thiazolo[4,5-c]pyridinium-2-yl}thiomethyl- 3-cephem-4-carboxylate trifluoroacetate Using 277 mg of p-methoxybenzyl 7-{(Z)-2-(2-tritylaminothiazol- 4-yl)-2-(1-tert-butoxycarbonyl-1-methylethoxyimino)acetamido}- 3-chloromethyl-3-cephem-4-carboxylate and 118 mg of 5-(2-fluoroethyl)-2-mercaptothiazolo[4,5-c]pyridinium trifluoroacetate in place of p-methoxybenzyl 7-{(Z)- 2-(2-tritylaminothiazol-4-yl)-2-methoxyiminoacetamido}- 3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 271 mg of the title compound in a yield of 74%.

NMR (CDCl$_3$) δ, 1.41 (9H, s), 1.62 (3H, s), 1.64 (3H, s), 3.47 (1H, d, J=18 Hz), 3.73 (1H, d, J=18 Hz), 3.79 (3H, s), 4.29 (1H, d, J=13 Hz), 4.83 (1H, d, J=13 Hz), 4.90–5.40 (7H, m), 5.97 (1H, dd, J=5 Hz, 9 Hz), 6.71 (1H, s), 6.85–6.90 (3H, m), 7.25–7.40 (17H, m), 8.17 (1H, d, J=9 Hz), 8.51 (1H, d, J=6 Hz), 9.19 (1H, d, J=6 Hz), 9.27 (1H, s)

(b) Preparation of 7-{(Z)-2-(2-aminothiazol-4-yl)-2-(1-carboxy- 1-methylethoxyimino)acetamido}-3-{5-(2-fluoroethyl)thiazolo[4,5-c]pyridinium- 2-yl}thiomethyl-3-cephem-4-carboxylate Using 271 mg of p-methoxybenzyl 7-{(Z)-2-(2-tritylaminothiazol- 4-yl)-2-(1-tert-butoxycarbonyl-1-methylethoxyimino)acetamido}- 3-{5-(2-fluoroethyl)thiazolo[4,5-c]pyridinium- 2-yl)thiomethyl-3-cephem-4-carboxylate trifluoroacetate as a starting material, the reaction and purification were carried out in the same manner as in Example 1(b) to obtain 107 mg of the title compound in the form of a sodium salt in a yield of 68%.

NMR (D$_2$O) δ, 1.48 (3H, s), 1.50 (3H, s), 3.47 (1H, d, J=18 Hz), 3.86 (1H, d, J=18 Hz), 4.12 (1H, d, J=13 Hz), 4.90–5.20 (6H, m), 5.78 (1H, d, J= 5 Hz), 6.98 (1H, s), 8.53 (1H, d, J=6 Hz), 8.62 (1H, d, J=6 Hz), 9.38 (1H, s)

EXAMPLE 24

(a) Preparation of p-methoxybenzyl 7-[(Z)-2-(2-tritylaminothiazol- 4-yl)-2-{(S)-1-diphenylmethoxycarbonylethoxyimino}acetamido]- 3-{5-(2-hydroxyethyl)thiazolo[4,5-c]pyridinium-2-yl)thiomethyl- 3-cephem-4-carboxylate trifluoroacetate Using 306 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate and 117 mg of 5-(2-hydroxyethyl)-2-mercaptothiazolo[4,5-c]pyridinium trifluoroacetate in place of p-methoxybenzyl 7-{(Z)- 2-(2-tritylaminothiazol-4-yl)-2-methoxyiminoacetamido}-3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 314 mg of the title compound in a yield of 80%.

NMR (CDCl$_3$) δ, 1.60 (3H, d, J=7 Hz), 3.42 (1H, d, J=18 Hz), 3.69 (1H, d, J=18 Hz), 3.77 (3H, s), 4.00–4.10 (2H, m), 4,22 (1H, d, J=13 Hz), 4.80–4.95 (3H, m), 4.97 (1H, d, J=5 Hz), 5.16 (1H, q, J=7 Hz), 5.22 (1H, d, J=12 Hz), 5.33 (1H, d, J=12 Hz), 5.87 (1H, dd, J= 5 Hz, 9 Hz), 6.72 (1H, s), 6.86 (2H, d, J=9 Hz), 6.89 (1H, s), 6.97 (1H, s), 7.20–7.35 (25H, m), 7.36 (2H, d, J=9 Hz), 8.02 (1H, d, J=9 Hz), 8.43 (1H, d, J=6 Hz), 8.92 (1H, d, J=6 Hz), 9.18 (1H, s)

(b) Preparation of 7-[(Z)-2-(2-aminothiazol-4-yl)-2-{(S)-1-carboxyethoxyimino}acetamido]- 3-{5-(2-hydroxyethyl)thiazolo[4,5-c]pyridinium-2-yl}thiomethyl-3-cephem-4-carboxylate Using 314 mg of p-methoxybenzyl 7-[(Z)-2-(2-tritylaminothiazol- 4-yl)-2-{(S)-1-diphenylmethoxycarbonylethoxyimino}acetamido]- 3-{5-(2-hydroxyethyl)thiazolo[4,5-c]pyridinium-2-yl)thiomethyl-3-cephem-4-carboxylate trifluoroacetate as a starting material, the reaction and purification were carried out in the same manner as in Example 1(b) to obtain 119 mg of the title compound in the form of a sodium salt in a yield of 72%.

NMR (D$_2$O) δ, 1.46 (3H, d, J=7 Hz), 3.48 (1H, d, J=18 Hz), 3.86 (1H, d, J=18 Hz), 4.05–4.20 (3H, m), 4.65 (1H, q, J=7 Hz), 4.80–4.90 (2H, m), 5.05 (1H, d, J=13 Hz), 5.14 (1H, d, J=5 Hz), 5.79 (1H, d, J=5 Hz), 7.02 (1H, s), 8.51 (1H, d, J=7 Hz), 8.60 (1H, d, J=7 Hz), 9.34 (1H, s)

EXAMPLE 25

(a) Preparation of p-methoxybenzyl 7-{(Z)-2-(2-tritylaminothiazol- 4-yl)-2-(1-tert-butoxycarbonyl-1-methylethoxyimino)acetamido}- 3-{5-(2-hydroxyethyl)thiazolo[4,5-c]pyridinium-2-yl}thiomethyl- 3-cephem-4-carboxylate trifluoroacetate Using 277 mg of p-methoxybenzyl 7-{(Z)-2-(2-tritylaminothiazol- 4-yl)-2-(1-tert-butoxycarbonyl-1-methylethoxyimino)acetamido}- 3-chloromethyl-3-cephem-4-carboxylate and 117 mg of 5-(2-hydroxyethyl)-2-mercaptothiazolo[4,5-c]pyridinium trifluoroacetate in place of p-methoxybenzyl 7-{(Z)- 2-(2-tritylaminothiazol-4-yl)-2-methoxyiminoacetamido}-3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 313 mg of the title compound in a yield of 86%.

NMR (CDCl$_3$) δ, 1.41 (9H, s), 1.58 (3H, s), 1.60 (3H, s), 3.47 (1H, d, J=18 Hz), 3.76 (1H, d, J=18 Hz), 3.79 (3H, s), 4.05–4.15 (2H, m), 4.24 (1H, d, J=13 Hz), 4.85 (1H, d, J=13 Hz), 4.90–5.00 (2H, m), 5.04 (1H, d, J=5 Hz), 5.23 (1H, d, J=12 Hz), 5.34 (1H, d, J=12 Hz), 5.94 (1H, dd, J=5 Hz, 9 Hz), 6.71 (1H, s), 6.87 (2H, d, J=9 Hz), 6.88 (1H, s), 7.20–7.35 (15H, m), 7.37 (2H, d, J=9 Hz), 8.19 (1H, d, J=9 Hz), 8.45 (1H, d, J=6 Hz), 8.96 (1H, d, J=6 Hz), 9.17 (1H, s)

(b) Preparation of 7-{(Z)-2-(2-aminothiazol-4-yl)-2-(1-carboxy- 1-methylethoxyimino)acetamido}-3-{5-(2-hydroxyethyl)thiazolo[4,5-c]pyridinium- 2-yl}thiomethyl-3-cephem-4-carboxylate Using 313 mg of p-methoxybenzyl 7-{(Z)-2-(2-tritylaminothiazol- 4-yl)-2-(1-tert-butoxycarbonyl-1-methylethoxyimino)acetamido}-3-{ 5-(2-hydroxyethyl)thiazolo[4,5-c]pyridinium-2-yl)thiomethyl-3-cephem-4-carboxylate trifluoroacetate as a starting material, the reaction and purification were carried out in the same manner as in Example 1(b) to obtain 101 mg of the title compound in the form of a sodium salt in a yield of 56%.

NMR (D$_2$O) δ, 1.49 (3H, s), 1.50 (3H, s), 3.47 (1H, d, J=18 Hz), 3.87 (1H, d, J=18 Hz), 4.05–4.15 (3H, m), 4.85–4.95 (2H, m), 5.06 (1H, d, J=13 Hz), 5.14 (1H, d, J=5 Hz), 5.78 (1H, d, J=5 Hz), 6.98 (1H, s), 8.52 (1H, d, J=6 Hz), 8.60 (1H, d, J=6 Hz), 9.35 (1H, s)

EXAMPLE 26

(a) Preparation of p-methoxybenzyl 7-[(Z)-2-(2-tritylaminothiazol- 4-yl)-2-{(S)-1-diphenylmethoxycarbonylethoxyimino}acetamido]- 3-(5-carbamoylmethylthiazolo[4,5-c]pyridinium-2-yl)thiomethyl- 3-cephem-4-carboxylate trifluoroacetate Using 306 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate and 117 mg of 5-carbamoylmethyl-2-mercaptothiazolo[4,5-c]pyridinium trifluoroacetate in place of p-methoxybenzyl 7-{(Z)- 2-(2-tritylaminothiazol-4-yl)-2-methoxyiminoacetamido}-3-chloromethyl- 3-cephem-4-carboxylate and 2-mercapto-4-methylthiazolo[5,4-b]pyridinium trifluoroacetate, respectively, the reaction and purification were carried out in the same manner as in Example 15(a) to obtain 229 mg of the title compound in a yield of 58%.

NMR (CDCl$_3$) δ, 1.61 (3H, d, J=7 Hz), 3.41 (1H, d, J=18 Hz), 3.65 (1H, d, J=18 Hz), 3.77 (3H, s), 4.29 (1H, d, J=13 Hz), 4.77 (1H, d, J=13 Hz), 4.95 (1H, d, J=5 Hz), 5.15 (1H, q, J=7 Hz), 5.22 (1H, d, J=12 Hz), 5.31 (1H, d, J=12 Hz), 5.85–6.20 (4H, m), 6.71 (1H, s), 6.85 (2H, d, J=9 Hz), 6.89 (1H, s), 7.00 (1H, s), 7.20–7.30 (25H, m), 7.34 (2H, d, J=9 Hz), 8.07 (1H, d, J=9 Hz), 8.34 (1H, d, J=7 Hz), 9.00–9.15 (2H, m), 9.40 (1H, s)

(b) Preparation of 7-[(Z)-2-(2-aminothiazol-4-yl)-2-{(S)-1-carboxyethoxyimino}acetamido]- 3-(5-carbamoylmethylthiazolo[4,5-c]pyridinium-2-yl)thiomethyl-3-cephem-4-carboxylate Using 229 mg of p-methoxybenzyl 7-[(Z)-2-(2-tritylaminothiazol- 4-yl)-2-{(S)-1-diphenylmethoxycarbonylethoxyimino}acetamido]- 3-(5-carbamoylmethylthiazolo[4,5-c]pyridinium-2-yl)thiomethyl-3-cephem-4-carboxylate trifluoroacetate as a starting material, the reaction and purification were carried out in the same manner as in Example 1(b) to obtain 82 mg of the title compound in the form of a sodium salt in a yield of 68%.

NMR (D₂O) δ, 1.46 (3H, d, J=7 Hz), 3.48 (1H, d, J=18 Hz), 3.86 (1H, d, J=18 Hz), 4.12 (1H, d, J= 13 Hz), 4.65 (1H, q, J=7 Hz), 5.06 (1H, d, J=13 Hz), 5.13 (1H, d, J=5 Hz), 5.60 (2H, s), 5.79 (1H, d, J=5 Hz), 7.01 (1H, s), 8.54 (2H, s), 9.30 (1H, s)

EXAMPLE 27

(a) Preparation of p-methoxybenzyl 7-{(Z)-2-(2-tritylaminothiazol- 4-yl)-2-(1-tert-butoxycarbonyl-1-methylethoxyimino)acetamido}- 3-(5-carbamoylmethylthiazolo[4,5-c]pyridinium-2-yl)thiomethyl-3-cephem-4-carboxylate trifluoroacetate Using 277 mg of p-methoxybenzyl 7-{(Z)-2-(2-tritylaminothiazol- 4-yl)-2-(1-tert-butoxycarbonyl-1-methylethoxyimino)acetamido}- 3-chloromethyl-3-cephem-4-carboxylate and 153 mg of 5-carbamoylmethyl-2-mercaptothiazolo-[4,5-c]pyridinium trifluoroacetate in place of p-methoxybenzyl 7-{(Z)- 2-(2-tritylaminothiazol-4-yl)-2-methoxyiminoacetamido}-3-chloromethyl- 3-cephem-4-carboxylate and 2-mercapto-4-methylthiazolo[5,4-b]pyridinium trifluoroacetate, respectively, the reaction and purification were carried out in the same manner as in Example 15(a) to obtain 223 mg of the title compound in a yield of 61%.

NMR (CDCl₃) δ, 1.39 (9H, s), 1.58 (3H, s), 1.59 (3H, s), 3.44 (1H, d, J=18 Hz), 3.73 (1H, d, J=18 Hz), 3.76 (3H, s), 4.28 (1H, d, J=13 Hz), 4.75 (1H, d, J=13 Hz), 5.01 (1H, d, J=5 Hz), 5.21 (1H, d, J=12 Hz), 5.30 (1H, d, J= 12 Hz), 5.90–6.00 (3H, m), 6.40 (1H, m), 6.70 (1H, s), 6.84 (2H, d, J=9 Hz), 6.94 (1H, s), 7.20–7.40 (17H, m), 8.15 (1H, d, J=9 Hz), 8.42 (1H, m), 8.95 (1H, m), 9.10 (1H, m), 9.40 (1H, s)

(b) Preparation of 7-{(Z)-2-(2-aminothiazol-4-yl)-2-(1-carboxy- 1-methylethoxyimino)acetamido}-3-(5-carbamoylmethylthiazolo[4,5-c]pyridinium- 2-yl}thiomethyl-3-cephem-4-carboxylate Using 223 mg of p-methoxybenzyl 7-{(Z)-2-(2-tritylaminothiazol- 4-yl)-2-(1-tert-butoxycarbonyl-1-methylethoxyimino)acetamido}- 3-(5-carbamoylthiazolo[4,5-c]pyridinium-2-yl)thiomethyl-3-cephem-4-carboxylate trifluoroacetate as a starting material, the reaction and purification were carried out in the same manner as in Example 1(b) to obtain 89 mg of the title compound in the form of a sodium salt in a yield of 68%.

NMR (D₂O) δ, 1.48 (3H, s), 1.50 (3H, s), 3.48 (1H, d, J=18 Hz), 3.86 (1H, d, J=18 Hz), 4.12 (1H, d, J=13 Hz), 5.06 (1H, d, J=13 Hz), 5.13 (1H, d, J=5 Hz), 5.60 (2H, s), 5.78 (1H, d, J=5 Hz), 6.98 (1H, s), 8.54 (2H, s), 9.31 (1H, s)

EXAMPLE 28

(a) Preparation of p-methoxybenzyl 7-{(Z)-2-(2-tritylaminothiazol- 4-yl)-2-methoxyiminoacetamido}-3-(5-methyloxazolo[4,5-c]pyridinium- 2-yl)thiomethyl-3-cephem-4-carboxylate trifluoroacetate Using 100 mg of 2-mercapto-5-methyloxazolo[4,5-c]pyridinium trifluoroacetate in place of 2-mercapto-4-methylthiazolo[5,4-b]pyridinium trifluoroacetate and 235 mg of p-methoxybenzyl 7-{(Z)-2-(2-trityl-aminothiazol-4-yl)-2-methoxyiminoacetamido}- 3-chloromethyl-3-cephem-4-carboxylate, the reaction and purification were carried out in the same manner as in Example 15(a) to obtain 261 mg of the title compound in a yield of 85%.

NMR (CDCl₃) δ, 3.51 (1H, d, J=18 Hz), 3.79 (1H, d, J=18 Hz), 4.30 (1H, d, J=13 Hz), 4.76 (3H, s), 4.88 (1H, d, J=13 Hz), 5.03 (1H, d, J=5 Hz), 5.21 (1H, d, J=12 Hz), 5.33 (1H, d, J= 12 Hz), 5.88 (1H, dd, J=5 Hz, 9 Hz), 6.73 (1H, s), 7.10–7.40 (15H, m), 8.03 (1H, d, J=9 Hz), 9.15 (1H, s), 9.32 (1H, d, J=9 Hz)

(b) Preparation of 7-{(Z)-2-(2-aminothiazol-4-yl)-2-methoxyiminoacetamido}- 3-(5-methyloxazolo[4,5-c]pyridinium-2-yl}thiomethyl-3-cephem-4-carboxylate Using 261 mg of p-methoxybenzyl 7-{(Z)-2-(2-tritylaminothiazol- 4-yl)-2-methoxyiminoacetamido}-3-(5-methyloxazolo[4,5-c]pyridinium- 2-yl)thiomethyl-3-cephem-4-carboxylate trifluoroacetate as a starting material, the reaction and purification were carried out in the same manner as in Example 1(b) to obtain 63 mg of the title compound in a yield of 45%.

NMR (D₂O) δ, 3.51 (1H, d, J=18 Hz), 3.93 (1H, d, J=18 Hz), 4.02 (3H, s), 4.14 (1H, d, J=13 Hz), 4.50 (3H, s), 4.95 (1H, d, J=13 Hz), 5.17 (1H, d, J=5 Hz), 5.82 (1H, d, J=5 Hz), 7.03 (1H, s), 8.15 (1H, d, J=6 Hz), 8.72 (1H, d, J=6 Hz), 9.19 (1H, s)

EXAMPLE 29

(a) Preparation of p-methoxybenzyl 7-{(Z)-2-(2-tritylaminothiazol- 4-yl)-2-diphenylmethoxycarbonylmethoxyiminoacetamido}- 3-(5-methyloxazolo[4,5-c]pyridinium-2-yl)thiomethyl-3-cephem-4-carboxylate trifluoroacetate Using 300 mg of p-methoxybenzyl 7-{(Z)-2-(2-tritylaminothiazol- 4-yl)-2-diphenylmethoxycarbonylmethoxyiminoacetamido}-3-chloromethyl-3-cephem-4-carboxylate and 100 mg of 2-mercapto-5-methyloxazolo[4,5-c]pyridinium trifluoroacetate in place of p-methoxybenzyl 7-{(Z)-2-(2-tritylaminothiazol- 4-yl)-2-methoxyiminoacetamido}-3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 302 mg of the title compound in a yield of 81%.

NMR (CDCl₃) δ, 3.43 (1H, d, J=18 Hz), 3.66 (1H, d, J=18 Hz), 3.78 (3H, s), 4.02 (2H, s), 4.30 (1H, d, J=13 Hz), 4.75 (1H, d, J=13 Hz), 4.96 (1H, d, J=5 Hz), 5.22 (1H, d, J=12 Hz), 5.34 (1H, d, J=12 Hz), 5.85 (1H, dd, J=5 Hz, 9 Hz), 6.77 (1H, s), 7.10–7.40 (15H, m), 8.05 (1H, d, J=9 Hz), 9.16 (1H, s), 9.35 (1H, d, J=9 Hz)

(b) Preparation of 7-{(Z)-2-(2-aminothiazol-4-yl)-2-carboxymethoxyiminoacetamido}- 3-(5-methyloxazolo[4,5-c]pyridinium-2-yl)thiomethyl-3-cephem-4-carboxylate Using 302 mg of p-methoxybenzyl 7-{(Z)-2-(2-tritylaminothiazol- 4-yl)-2-diphenylcarbonylmethoxyiminoacetamido}-3-(5-methyloxazolo[4,5-c]pyridinium-2-yl)thiomethyl-3-cephem-4-carboxylate trifluoroacetate as a starting material, the reaction and purification were carried out in the same manner as in Example 1(b) to obtain 88 mg of the title compound in the form of a sodium salt in a yield of 58%.

NMR (D₂O) δ, 3.75 (1H, d, J=18 Hz), 4.12 (1H, d, J=18 Hz), 4.38 (1H, d, J=12 Hz), 4.72 (3H, s), 4.84 (2H, s), 5.13 (1H, d, J=12 Hz), 5.41 (1H, d, J=5 Hz), 6.05 (1H, d, J=5 Hz), 7.29 (1H, s), 8.39 (1H, d, J=6 Hz), 8.96 (1H, d, J=6 Hz), 9.42 (1H, s)

EXAMPLE 30

(a) Preparation of p-methoxybenzyl 7-[(Z)-2-(2-tritylaminothiazol- 4-yl)-2-{(S)-1-diphenylmethoxycarbonylethoxyimino}acetamido]- 3-(5-methyloxazolo[4,5-c]pyridinium-2-yl)thiomethyl-3-cephem-4-carboxylate trifluoroacetate Using 303 mg of p-methoxybenzyl 7-[(Z)-2-(2-tritylaminothiazol-4-yl)-2-{(S)-1-diphenylmethoxycarbonylethoxyimino}acetamido]- 3-chloromethyl-3-cephem-4-carboxylate and 100 mg of 2-mercapto-5-methyloxazolo[4,5-c]pyridinium trifluoroacetate in place of p-methoxybenzyl 7-{(Z)-2-(2-tritylaminothiazol-4-yl)-2-methoxyiminoacetamido} -3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 331 mg of the title compound in a yield of 88%.

NMR (CDCl$_3$) δ, 1.58 (3H, d, J=7 Hz), 3.42 (1H, d, J=18 Hz), 3.63 (1H, d, J=18 Hz), 3.78 (3H, s), 4.29 (1H, d, J=13 Hz), 4.78 (1H, d, J=13 Hz), 4.98 (1H, d, J=5 Hz), 5.14 (1H, q, J=7 Hz), 5.25 (1H, d, J=12 Hz), 5.33 (1H, d, J=12 Hz), 5.82 (1H, dd, J=5 Hz, 9 Hz), 6.72 (1H, s), 7.10–7.40 (15H, m), 8.05 (1H, d, J=9 Hz), 9.17 (1H, s), 9.35 (1H, d, J=9 Hz)

(b) Preparation of 7-[(Z)-2-(2-aminothiazol-4-yl)-2-{(S)-1-carboxyethoxyimino}acetamido]- 3-(5-methyloxazolo[4,5-c]-pyridinium-2-yl)thiomethyl-3-cephem-4-carboxylate Using 331 mg of p-methoxybenzyl 7-[(Z)-2-(2-tritylaminothiazol- 4-yl)-2-{(S)-1-diphenylmethoxycarbonylethoxyimino}acetamido]- 3-(5-methyloxazolo[4,5-c]pyridinium-2-yl)thiomethyl-3-cephem-4-carboxylate trifluoroacetate as a starting material, the reaction and purification were carried out in the same manner as in Example 1(b) to obtain 98 mg of the title compound in the form of a sodium salt in a yield of 58%.

NMR (D$_2$O) δ, 1.46 (3H, d, J=7 Hz), 3.49 (1H, d, J=18 Hz), 3.88 (1H, d, J=14 Hz), 4.47 (3H, s), 4.66 (1H, q, J=7 Hz), 5.17 (1H, d, J=5 Hz), 5.79 (1H, d, J=5 Hz), 6.97 (1H, s), 8.12 (1H, d, J=6 Hz), 8.69 (1H, d, J=6 Hz), 9.15 (1H, s)

EXAMPLE 31

Preparation of 7-{(Z)-2-(5-aminothiadiazol-3-yl)-2-methoxyiminoacetamido}- 3-(5-methyloxazolo[4,5-c]pyridinium-2-yl)thiomethyl-3-cephem-4-carboxylate Using 100 mg of 2-mercapto-5-methyloxazolo[4,5-c]pyridinium trifluoroacetate in place of 2-mercapto-5-methylthiazolo[4,5-c]pyridinium chloride and 163 mg of p-methoxybenzyl 7-{(Z)-2-(5-aminothiadiazol-3-yl)-2-methoxyiminoacetamido}- 3-chloromethyl-3-cephem-4-carboxylate, the reaction and purification were carried out in the same manner as in Example 6 to obtain 62 mg of the title compound in the form of a sodium salt in a yield of 31%.

NMR (D$_2$O) δ, 3.48 (1H, d, J=18 Hz), 3.90 (1H, d, J=18 Hz), 4.01 (1H, d, J=14 Hz), 4.08 (3H, d), 4.93 (1H, d, J=14 Hz), 5.13 (1H, d, J=5 Hz), 5.82 (1H, d, J=5 Hz), 8.13 (1H, d, J=6 Hz), 8.71 (1H, d, J=6 Hz), 9.17 (1H, s)

EXAMPLE 32

(a) Preparation of p-methoxybenzyl 7-[(Z)-2-(2-tritylaminothiazol- 4-yl)-2-{(S)-1-diphenylmethoxycarbonylethoxyimino}acetamido]-3-(5-methylthiazolo[ 4,5-d]pyridazinium-2-yl)thiomethyl-3-cephem-4-carboxylate trifluoroacetate Using 170 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate and 60 mg of 2-mercapto-5-methylthiazolo[4,5-d]pyridazinium trifluoroacetate in place of p-methoxybenzyl 7-{(Z)-2-(2-tritylaminothiazol- 4-yl)-2-methoxyiminoacetamido}-3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 198 mg of the title compound in a yield of 93%.

NMR (CDCl$_3$) δ, 1.60 (3H, d, J=7 Hz), 3.45 (1H, d, J=18 Hz), 3.76 (1H, d, J=18 Hz), 3.79 (3H, s), 4.25 (1H, d, J=13 Hz), 4.65 (3H, s), 4.94 (1H, d, J=5 Hz), 5.03 (1H, d, J=13 Hz), 5.10–5.40 (3H, m), 5.85 (1H, dd, J=5 Hz, 9 Hz), 6.72 (1H, s), 6.80–7.45 (31H, m), 8.00 (1H, d, J=9 Hz), 9.92 (1H, s), 10.17 (1H, s)

(b) Preparation of 7-[(Z)-2-(2-aminothiazol-4-yl)-2-{(S)-1-carboxyethoxyimino}acetamido]- 3-(5-methylthiazolo[4,5-d]pyridazinium-2-yl)thiomethyl-3-cephem-4-carboxylate Using 198 mg of p-methoxybenzyl 7-[(Z)-2-(2-tritylaminothiazol- 4-yl)-2-{(S)-1-diphenylmethoxycarbonylethoxyimino}acetamido]- 3-(5-methylthiazolo[4,5-d]pyridazinium-2-yl)thiomethyl-3-cephem-4-carboxylate trifluoroacetate as a starting material, the reaction and purification were carried out in the same manner as in Example 1(b) to obtain 26 mg of the title compound in the form of a sodium salt in a yield of 25%.

NMR (D$_2$O) δ, 1.49 (3H, d, J=7 Hz), 3.49 (1H, d, J=18 Hz), 3.87 (1H, d, J=18 Hz), 4.20 (1H, d, J= 13 Hz), 4.68 (1H, d, J=13 Hz), 4.71 (3H, s), 5.16 (1H, d, J=5 Hz), 5.81 (1H, d, J=5 Hz), 7.04 (1H, s), 9.83 (1H, s), 10.03 (1H, s)

EXAMPLE 33

(a) Preparation of p-methoxybenzyl 7-[(Z)-2-(2-tritylaminothiazol- 4-yl)-2-{(S)-1-diphenylmethoxycarbonylethoxyimino}acetamido]- 3-(5,5-dimethyl-4H,6H,7H-thiazolo[5,4-c]pyridinium-2-yl)thiomethyl-3-cephem-4-carboxylate trifluoroacetate Using 306 mg of p-methoxybenzyl 7-[(Z)-2-(2-tritylaminothiazol- 4-yl)-2-{(S)-1-diphenylmethoxycarbonylethoxyimino}acetamido]- 3-chloromethyl-3-cephem-4-carboxylate and 113 mg of 5,5-methyl-2-mercapto-4H,6H,7H-thiazolo[4,5-c]pyridinium trifluoroacetate in place of p-methoxybenzyl 7-{(Z)- 2-(2-tritylaminothiazol-4-yl)-2-methoxyiminoacetamido}- 3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 242 mg of the title compound in a yield of 62%.

NMR (CDCl$_3$) δ, 1.60 (3H, d, J=7 Hz), 3.10 (2H, m), 3.37 (1H, d, J=18 Hz), 3.50–3.60 (7H, m), 3.81 (3H, m), 3.90–4.05 (2H, m), 4.06 (1H, d, J=13 Hz), 4.49 (1H, d, J=13 Hz), 4.95–5.00 (3H, m), 5.14 (1H, d, J=12 Hz), 5.17 (1H, q, J=7 Hz), 5.25 (1H, d, J=12 Hz), 5.85 (1H, dd, J=5 Hz, 9 Hz), 6.73 (1H, s), 6.89 (1H, s), 6.90 (2H, d, J=9 Hz), 6.98 (1H, s), 7.20–7.40 (27H, m), 8.00 (1H, d, J=9 Hz)

(b) Preparation of 7-[(Z)-2-(2-aminothiazol-4-yl)-2-{(S)-1-carboxyethoxyimino}acetamido]- 3-(5,5-dimethyl-4H,6H, 7H-thiazolo[5,4-c]pyridinium- 2-yl)thiomethyl-3-cephem-4-carboxylate Using 242 mg of p-methoxybenzyl 7-[(Z)-2-(2-tritylaminothiazol- 4-yl)-2-{(S)-1-diphenylmethoxycarbonylethoxyimino}acetamido]- 3-(5,5-dimethyl-4H,6H,7H-thiazolo[5,4-c]pyridinium-2-yl)thiomethyl-3-cephem-4-carboxylate trifluoroacetate as a starting material, the reaction and purification were carried out in the same manner as in Example 1(b) to obtain 79 mg of the title compound in the form of a sodium salt in a yield of 63%.

NMR (D$_2$O) δ, 1.46 (3H, d, J=7 Hz), 3.20–3.30 (8H, m), 3.41 (1H, d, J=18 Hz), 3.75–3.90 (4H, m), 4.57 (1H, d, J=13 Hz), 4.65 (1H, q, J=7 Hz), 4.73 (2H, s), 5.18 (1H, d, J=5 Hz), 5.77 (1H, d, J=5 Hz), 7.04 (1H, s)

EXAMPLE 34

(a) Preparation of p-methoxybenzyl 7-[(Z)-2-(2-tritylaminothiazol-4-yl)-2-{(S)-1-diphenylmethoxycarbonylethoxyimino}acetamido]-3-(1,5-dimethylimidazolo[4,5-c]pyridinium-2-yl)thiomethyl-3-cephem-4-carboxylate trifluoroacetate Using 306 mg of p-methoxybenzyl 7-[(Z)-2-(2-tritylaminothiazol-4-yl)-2-{(S)-1-diphenylmethoxycarbonylethoxyimino}acetamido]-3-chloromethyl-3-cephem-4-carboxylate and 153 mg of 1,5-dimethyl-2-mercaptoimidazolo[4,5-c]pyridinium trifluoroacetate in place of p-methoxybenzyl 7-{(Z)-2-(2-tritylaminothiazol-4-yl)-2-methoxyiminoacetamido}-3-chloromethyl-3-cephem-4-carboxylate and 2-mercapto-4-methylthiazolo[5,4-b]pyridinium trifluoroacetate, respectively, the reaction and purification were carried out in the same manner as in Example 15(a) to obtain 334 mg of the title compound in a yield of 88%.

NMR (CDCl$_3$) δ, 1.60 (3H, d, J=7 Hz), 3.46 (1H, d, J=18 Hz), 3.71 (1H, d, J=18 Hz), 3.79 (3H, s), 3.85 (3H, s), 4.20 (1H, d, J=13 Hz), 4.50 (3H, s), 4.87 (1H, d, J=13 Hz), 4.97 (1H, d, J=5 Hz), 5.16 (1H, q, J=7 Hz), 5.20 (1H, d, J=12 Hz), 5.39 (1H, d, J=13 Hz), 5.86 (1H, dd, J=5 Hz, 9 Hz), 6.72 (1H, s), 6.89 (2H, d, J=9 Hz), 6.90 (1H, s), 6.98 (1H, s), 7.20–7.35 (25H, m), 7.39 (2H, d, J= 9 Hz), 8.03 (1H, d, J=9 Hz), 8.21 (1H, d, J=6 Hz), 8.51 (1H, s), 8.99 (1H, d, J=6 Hz)

(b) Preparation of 7-[(Z)-2-(2-aminothiazol-4-yl)-2-{(S)-1-carboxyethoxyimino}acetamido]-3-(1,5-dimethylimidazolo[4,5-c]pyridinium-2-yl)thiomethyl-3-cephem-4-carboxylate Using 334 mg of p-methoxybenzyl 7-[(Z)-2-(2-tritylaminothiazol-4-yl)-2-{(S)-1-diphenylmethoxycarbonylethoxyimino}acetamido]-3-(1,5-dimethylimidazolo[4,5-c]pyridinium-2-yl)thiomethyl-3-cephem-4-carboxylate trifluoroacetate as a starting material, the reaction and purification were carried out in the same manner as in Example 1(b) to obtain 87 mg of the title compound in the form of a sodium salt in a yield of 51%.

NMR (D$_2$O) δ, 1.45 (3H, d, J=7 Hz), 3.49 (1H, d, J=18 Hz), 3.83 (1H, d, J=18 Hz), 3.86 (3H, s), 4.18 (1H, d, J=13 Hz), 4.40 (3H, s), 4.65 (1H, q, J=7 Hz), 4.69 (1H, d, J=13 Hz), 5.16 (1H, d, J=5 Hz), 5.78 (1H, d, J=5 Hz), 6.99 (1H, s), 7.91 (1H, d, J=7 Hz), 8.41 (1H, d, J=7 Hz), 8.99 (1H, s)

While the invention has been described in detail and with reference to specific examples thereof, it will be apparent to one skilled in the art that various changes and modifications can be made therein without departing from the spirit and scope thereof.

What is claimed is:

1. A cephalosporin derivative represented by formula (I):

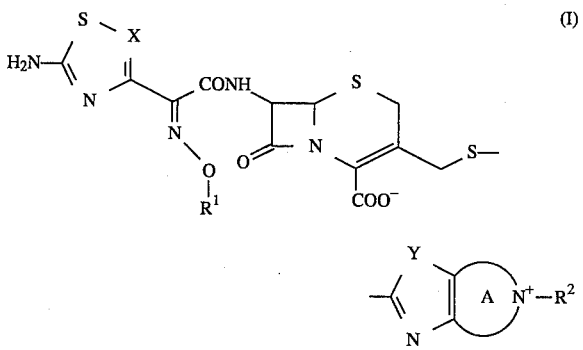

wherein X is a carbon atom or a nitrogen atom; Y is a sulfur atom, an oxygen atom or a nitrogen atom substituted with a substituted or unsubstituted lower alkyl group; $R^1$ is a hydrogen atom, a lower alkyl group or a substituted lower alkyl group; $R^2$ is a lower alkyl group, a substituted lower alkyl group, a lower alkylene group or a substituted lower alkylene group, wherein said substituted lower alkyl and alkylene groups are alkyl and alkylene groups each substituted with a substituent selected from the group consisting of a halogen atom, a hydroxyl group, a carboxyl group, a carbamoyl group, an amino group, and an alkylamino group having 1 to 4 -carbon atoms, and said substituents may be substituted with a member selected from the group consisting of an alkyl group having 1 to 4 -carbon atoms, an alkylene group having 1 to 4 -carbon atoms, and an aralkyl group having 7 to 10 -carbon atoms; and A is an unsaturated six-membered heterocyclic ring containing at least one nitrogen atom, wherein said heterocyclic ring is selected from the group consisting of pyridine, pyrimidine, pyrazine, pyridazine, dihydro derivatives of pyridazine, tetrahydro derivatives of pyridazine, thiazine, thiadiazine, oxazine and oxadiazine, or a pharmaceutically acceptable salt thereof.

2. The cephalosporin derivative according to claim 1, wherein the lower alkyl and alkylene groups have 1 to 4 -carbon atoms.

3. An antibacterial composition which comprises a cephalosporin derivative represented by formula (I):

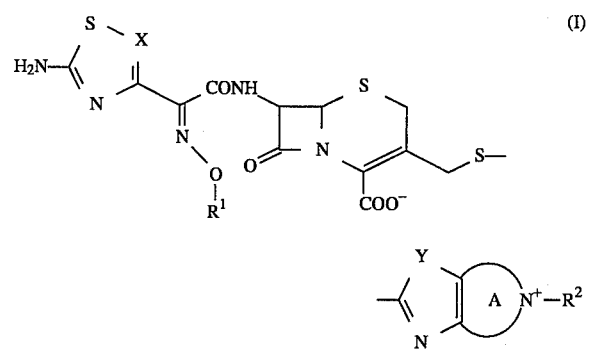

wherein X is a carbon atom or a nitrogen atom; Y is a sulfur atom, an oxygen atom or a substituted or unsubstituted lower alkyl group; $R^1$ is a hydrogen atom, a lower alkyl group or a substituted lower alkyl group; $R^2$ is a lower alkyl group, a substituted lower alkyl group, a lower alkylene group or substituted lower alkylene group, wherein said substituted lower alkyl and alkylene groups are alkyl and alkylene groups each substituted with a substituent selected from the group consisting of a halogen atom, a hydroxyl group, a carboxyl group, a carbamoyl group, an amino group, and an alkylamino group having 1 to 4 -carbon atoms, and said substituent may be substituted with a member selected from the group consisting of an alkyl group having 1 to 4 -carbon atoms, an alkylene group having 1 to 4 -carbon atoms and an aralkyl group having 6 to 10 carbon atoms; and A is an unsaturated six-membered heterocyclic ring containing at least one nitrogen atom, wherein said heterocyclic ring is selected from the group consisting of pyridine, pyrimidine, pyrazine, pyridazine, dihydro derivatives of pyridazine, tetraphydro derivatives of pyridazine, thiazine, thiadiazine, oxazine and oxadiazine, or a pharmaceutically acceptable salt thereof as an active ingredient, and a pharmaceutically acceptable carrier.

4. The antibacterial composition according to claim 3, wherein the lower alkyl and alkylene groups have 1 to 4 -carbon atoms.

* * * * *